(12) United States Patent
Franklin et al.

(10) Patent No.: US 9,199,069 B2
(45) Date of Patent: Dec. 1, 2015

(54) IMPLANTABLE INJECTION PORT

(75) Inventors: Ethan Franklin, Goleta, CA (US); Justin Schwab, Santa Barbara, CA (US); Zachary P. Dominguez, Santa Barbara, CA (US)

(73) Assignee: Apollo Endosurgery, Inc., Austin, TX (US)

( * ) Notice: Subject to any disclaimer, the term of this patent is extended or adjusted under 35 U.S.C. 154(b) by 361 days.

(21) Appl. No.: 13/277,802

(22) Filed: Oct. 20, 2011

(65) Prior Publication Data

US 2013/0102840 A1 Apr. 25, 2013

(51) Int. Cl.
*A61M 39/04* (2006.01)
*A61M 39/02* (2006.01)
*A61M 39/00* (2006.01)
*A61F 5/00* (2006.01)

(52) U.S. Cl.
CPC .......... *A61M 39/0208* (2013.01); *A61F 5/0056* (2013.01); *A61M 2039/0063* (2013.01); *A61M 2039/0072* (2013.01); *Y10T 156/1005* (2015.01)

(58) Field of Classification Search
CPC ............ A61M 39/0208; A61M 39/04; A61M 2039/0211; A61M 2039/0214; A61M 2039/022; A61M 2039/0223; A61M 2039/0226; A61M 2039/0232; A61M 2039/0235; A61M 5/14276
USPC .................. 600/37; 604/288.01–288.04, 175
See application file for complete search history.

(56) References Cited

U.S. PATENT DOCUMENTS

| | | |
|---|---|---|
| 586,113 A | 7/1897 | Bott |
| 2,163,048 A | 6/1939 | McKee |
| 2,737,954 A | 3/1956 | Knapp |
| 3,371,352 A | 3/1968 | Siposs et al. |
| 3,569,660 A | 3/1971 | Houldcroft |
| 3,587,115 A | 6/1971 | Shiley |
| 3,596,660 A | 8/1971 | Melone |
| 3,667,081 A | 6/1972 | Burger |
| 3,688,764 A | 9/1972 | Reed |
| 3,840,018 A | 10/1974 | Heifetz |

(Continued)

FOREIGN PATENT DOCUMENTS

| | | |
|---|---|---|
| CN | 1250382 | 4/2000 |
| CN | 1367670 | 9/2002 |

(Continued)

OTHER PUBLICATIONS http://en/wikipedia.org/Injection_Molding.

(Continued)

*Primary Examiner* — Charles A Marmor, II
*Assistant Examiner* — Thaddeus Cox
(74) *Attorney, Agent, or Firm* — Gordon & Jacobson, P.C.

(57) ABSTRACT

Injection ports are disclosed for use with a gastric band for the treatment of obesity. An injection port may include a septum having a top surface, a bottom surface, and a side wall connecting the top surface to the bottom surface. The injection port may also include a housing including a first inner side wall being tapered inwards such that an opening defined at a first end is larger than an opening defined at a second end, the tapering of the first inner side wall being used to secure the septum within the housing. The housing may further include a second inner side wall having a first end and a second end, the first end of the second inner side wall joined to the second end of the first inner side wall, and a bottom surface joined to the second end of the second inner side wall.

3 Claims, 18 Drawing Sheets

(56) References Cited

U.S. PATENT DOCUMENTS

| | | | |
|---|---|---|---|
| 3,958,562 | A | 5/1976 | Hakim et al. |
| 3,971,376 | A | 7/1976 | Wichterle |
| 4,019,499 | A | 4/1977 | Fitzgerald |
| 4,118,805 | A | 10/1978 | Reimels |
| 4,151,835 | A | 5/1979 | Showell et al. |
| 4,161,943 | A | 7/1979 | Nogier |
| 4,164,943 | A | 8/1979 | Hill et al. |
| 4,190,040 | A | 2/1980 | Schulte |
| 4,233,992 | A | 11/1980 | Bisping |
| 4,265,252 | A | 5/1981 | Chubbuck et al. |
| 4,280,722 | A | 7/1981 | Guptil et al. |
| 4,413,985 | A | 11/1983 | Wellner et al. |
| 4,474,572 | A | 10/1984 | McNaughton et al. |
| 4,502,335 | A | 3/1985 | Wamstad et al. |
| 4,543,088 | A | 9/1985 | Bootman et al. |
| 4,557,722 | A | 12/1985 | Harris |
| 4,569,675 | A | 2/1986 | Prosl et al. |
| 4,588,394 | A | 5/1986 | Schulte et al. |
| 4,592,339 | A | 6/1986 | Kuzmak et al. |
| 4,592,355 | A | 6/1986 | Antebi |
| 4,634,427 | A | 1/1987 | Hannula et al. |
| 4,655,765 | A | 4/1987 | Swift |
| 4,673,394 | A | 6/1987 | Fenton, Jr. et al. |
| 4,692,146 | A | 9/1987 | Hilger |
| 4,696,288 | A | 9/1987 | Kuzmak et al. |
| 4,704,103 | A | 11/1987 | Stober et al. |
| 4,710,174 | A | 12/1987 | Moden et al. |
| 4,738,657 | A | 4/1988 | Hancock et al. |
| 4,767,410 | A | 8/1988 | Moden et al. |
| 4,772,270 | A | 9/1988 | Wiita et al. |
| 4,778,452 | A | 10/1988 | Moden et al. |
| 4,781,680 | A | 11/1988 | Redmond et al. |
| 4,796,641 | A | 1/1989 | Mills et al. |
| 4,802,885 | A | 2/1989 | Weeks et al. |
| 4,832,054 | A | 5/1989 | Bark |
| 4,840,615 | A | 6/1989 | Hancock et al. |
| 4,850,227 | A | 7/1989 | Luettgen et al. |
| 4,858,623 | A | 8/1989 | Bradshaw et al. |
| 4,861,341 | A | 8/1989 | Woodburn |
| 4,881,939 | A | 11/1989 | Newman |
| 4,886,501 | A | 12/1989 | Johnston et al. |
| 4,902,278 | A | 2/1990 | Maget et al. |
| 4,904,241 | A | 2/1990 | Bark |
| 4,913,702 | A | 4/1990 | Yum et al. |
| 4,915,690 | A | 4/1990 | Cone et al. |
| 4,929,230 | A | 5/1990 | Pfleger |
| 4,929,236 | A | 5/1990 | Sampson |
| 4,966,588 | A | 10/1990 | Rayman et al. |
| 4,967,755 | A | 11/1990 | Pohndorf |
| 4,978,338 | A | 12/1990 | Melsky et al. |
| 5,006,115 | A | 4/1991 | McDonald |
| 5,013,298 | A | 5/1991 | Moden et al. |
| 5,026,344 | A | 6/1991 | Dijkstra et al. |
| 5,041,098 | A | 8/1991 | Loiterman et al. |
| 5,045,060 | A | 9/1991 | Melsky et al. |
| 5,074,868 | A | 12/1991 | Kuzmak |
| 5,090,954 | A | 2/1992 | Geary |
| 5,092,897 | A | 3/1992 | Forte |
| 5,094,244 | A | 3/1992 | Callahan et al. |
| 5,108,377 | A | 4/1992 | Cone et al. |
| 5,125,408 | A | 6/1992 | Basser |
| 5,133,753 | A | 7/1992 | Bark et al. |
| 5,137,529 | A | 8/1992 | Watson et al. |
| 5,147,483 | A | 9/1992 | Melsky et al. |
| 5,152,747 | A | 10/1992 | Olivier |
| 5,167,638 | A | 12/1992 | Felix et al. |
| 5,185,003 | A | 2/1993 | Brethauer |
| 5,207,644 | A | 5/1993 | Strecker |
| 5,213,574 | A | 5/1993 | Tucker |
| 5,226,429 | A | 7/1993 | Kuzmak |
| 5,226,894 | A | 7/1993 | Haber et al. |
| 5,250,026 | A | 10/1993 | Ehrlich et al. |
| 5,273,537 | A | 12/1993 | Haskvitz et al. |
| 5,281,205 | A | 1/1994 | McPherson |
| 5,284,479 | A | 2/1994 | de Jong |
| 5,318,545 | A | 6/1994 | Tucker |
| 5,336,194 | A | 8/1994 | Polaschegg et al. |
| 5,337,747 | A | 8/1994 | Neftel |
| 5,360,407 | A | 11/1994 | Leonard et al. |
| 5,368,040 | A | 11/1994 | Carney |
| 5,387,192 | A | 2/1995 | Glantz et al. |
| 5,391,164 | A | 2/1995 | Giampapa |
| 5,449,368 | A | 9/1995 | Kuzmak |
| 5,476,460 | A | 12/1995 | Montalvo |
| 5,514,174 | A | 5/1996 | Heil, Jr. et al. |
| 5,540,648 | A | 7/1996 | Yoon |
| 5,556,388 | A | 9/1996 | Johlin, Jr. |
| 5,558,641 | A | 9/1996 | Glantz et al. |
| 5,562,617 | A | 10/1996 | Finch, Jr. et al. |
| 5,571,104 | A | 11/1996 | Li |
| 5,575,777 | A | 11/1996 | Cover et al. |
| 5,601,604 | A | 2/1997 | Vincent |
| 5,637,102 | A | 6/1997 | Tolkoff et al. |
| 5,653,755 | A | 8/1997 | Ledergerber |
| 5,658,298 | A | 8/1997 | Vincent et al. |
| 5,674,397 | A | 10/1997 | Pawlak et al. |
| 5,683,447 | A | 11/1997 | Bush et al. |
| 5,688,237 | A | 11/1997 | Rozga et al. |
| 5,695,490 | A | 12/1997 | Flaherty et al. |
| 5,716,342 | A | 2/1998 | Dumbraveanu et al. |
| 5,718,682 | A | 2/1998 | Tucker |
| 5,722,957 | A | 3/1998 | Steinbach |
| 5,748,200 | A | 5/1998 | Funahashi |
| 5,810,735 | A | 9/1998 | Halperin et al. |
| 5,814,019 | A | 9/1998 | Steinbach et al. |
| 5,833,654 | A | 11/1998 | Powers et al. |
| 5,843,033 | A | 12/1998 | Ropiak |
| RE36,176 | E | 3/1999 | Kuzmak |
| 5,883,654 | A | 3/1999 | Katsuyama |
| 5,902,598 | A | 5/1999 | Chen et al. |
| 5,906,596 | A | 5/1999 | Tallarida |
| 5,910,149 | A | 6/1999 | Kuzmak |
| 5,911,704 | A | 6/1999 | Humes |
| 5,931,829 | A | 8/1999 | Burbank et al. |
| 5,932,460 | A | 8/1999 | Mills et al. |
| 5,935,083 | A | 8/1999 | Williams |
| 5,938,669 | A | 8/1999 | Klaiber et al. |
| 5,951,512 | A | 9/1999 | Dalton |
| 6,024,704 | A | 2/2000 | Meador et al. |
| 6,030,369 | A | 2/2000 | Engelson et al. |
| 6,039,712 | A | 3/2000 | Fogarty et al. |
| 6,074,341 | A | 6/2000 | Anderson et al. |
| 6,090,066 | A | 7/2000 | Schnell |
| 6,098,405 | A | 8/2000 | Miyata et al. |
| 6,102,678 | A | 8/2000 | Peclat |
| 6,102,922 | A | 8/2000 | Jakobsson et al. |
| 6,123,700 | A | 9/2000 | Mills et al. |
| 6,152,885 | A | 11/2000 | Taepke |
| 6,171,252 | B1 | 1/2001 | Roberts |
| 6,183,449 | B1 | 2/2001 | Sibbitt |
| 6,213,973 | B1 | 4/2001 | Eliasen et al. |
| 6,221,024 | B1 | 4/2001 | Miesel |
| 6,234,973 | B1 | 5/2001 | Meador et al. |
| 6,258,079 | B1 | 7/2001 | Burbank et al. |
| 6,264,676 | B1 | 7/2001 | Gellman et al. |
| 6,270,475 | B1 | 8/2001 | Bestetti et al. |
| 6,283,949 | B1 | 9/2001 | Roorda |
| 6,321,124 | B1 | 11/2001 | Cigaina |
| 6,349,740 | B1 | 2/2002 | Cho et al. |
| 6,432,040 | B1 | 8/2002 | Meah |
| 6,450,946 | B1 | 9/2002 | Forsell |
| 6,453,907 | B1 | 9/2002 | Forsell |
| 6,454,699 | B1 | 9/2002 | Forsell |
| 6,459,917 | B1 | 10/2002 | Gowda et al. |
| 6,461,293 | B1 | 10/2002 | Forsell |
| 6,464,628 | B1 | 10/2002 | Forsell |
| 6,470,213 | B1 | 10/2002 | Alley |
| 6,470,892 | B1 | 10/2002 | Forsell |
| 6,478,783 | B1 | 11/2002 | Moorehead |
| 6,511,490 | B2 | 1/2003 | Robert |
| 6,547,801 | B1 | 4/2003 | Dargent et al. |
| 6,572,587 | B2 | 6/2003 | Lerman et al. |
| 6,589,184 | B2 | 7/2003 | Noren et al. |
| 6,648,849 | B2 | 11/2003 | Tenhuisen et al. |

(56) References Cited

U.S. PATENT DOCUMENTS

| | | |
|---|---|---|
| 6,666,845 B2 | 12/2003 | Hooper et al. |
| 6,689,100 B2 | 2/2004 | Connelly et al. |
| 6,723,053 B2 | 4/2004 | Ackerman et al. |
| 6,733,519 B2 | 5/2004 | Lashinski et al. |
| 6,792,309 B1 | 9/2004 | Noren |
| 6,810,880 B1 | 11/2004 | Jennings, Jr. et al. |
| 6,813,964 B1 | 11/2004 | Clark et al. |
| 6,860,857 B2 | 3/2005 | Noren et al. |
| 6,915,162 B2 | 7/2005 | Noren et al. |
| 6,921,267 B2 | 7/2005 | van Oostrom et al. |
| 6,929,631 B1 | 8/2005 | Brugger et al. |
| 6,939,299 B1 | 9/2005 | Petersen et al. |
| 6,953,444 B2 | 10/2005 | Rosenberg |
| 6,964,204 B2 | 11/2005 | Clark et al. |
| 6,966,875 B1 | 11/2005 | Longobardi |
| 6,997,914 B2 | 2/2006 | Smith et al. |
| 7,017,583 B2 | 3/2006 | Forsell |
| 7,020,531 B1 | 3/2006 | Colliou et al. |
| 7,056,286 B2 | 6/2006 | Ravenscroft et al. |
| 7,063,669 B2 | 6/2006 | Brawner et al. |
| 7,073,387 B2 | 7/2006 | Zdeblick et al. |
| 7,082,843 B2 | 8/2006 | Clark et al. |
| 7,131,945 B2 | 11/2006 | Fink et al. |
| 7,144,400 B2 | 12/2006 | Byrum et al. |
| 7,149,587 B2 | 12/2006 | Wardle et al. |
| 7,191,007 B2 | 3/2007 | Desai et al. |
| 7,195,774 B2 | 3/2007 | Carvalho et al. |
| 7,223,239 B2 | 5/2007 | Schulze et al. |
| 7,226,419 B2 | 6/2007 | Lane et al. |
| 7,261,003 B2 | 8/2007 | McDonald et al. |
| 7,267,645 B2 | 9/2007 | Anderson et al. |
| 7,282,023 B2 | 10/2007 | Frering |
| 7,311,716 B2 | 12/2007 | Byrum |
| 7,311,717 B2 | 12/2007 | Egle |
| 7,351,198 B2 | 4/2008 | Byrum et al. |
| 7,351,226 B1 | 4/2008 | Herskowitz |
| 7,351,240 B2 | 4/2008 | Hassler, Jr. et al. |
| 7,353,747 B2 | 4/2008 | Swayze et al. |
| 7,364,542 B2 | 4/2008 | Jambor et al. |
| 7,367,937 B2 | 5/2008 | Jambor et al. |
| 7,374,557 B2 | 5/2008 | Conlon et al. |
| 7,374,565 B2 | 5/2008 | Hassler, Jr. et al. |
| 7,390,294 B2 | 6/2008 | Hassler, Jr. |
| 7,413,547 B1 | 8/2008 | Lichtscheidl et al. |
| 7,416,528 B2 | 8/2008 | Crawford et al. |
| 7,437,951 B2 | 10/2008 | McDonald et al. |
| 7,438,718 B2 | 10/2008 | Milliman et al. |
| 7,445,614 B2 | 11/2008 | Bunodiere et al. |
| 7,468,038 B2 | 12/2008 | Ye et al. |
| 7,500,944 B2 | 3/2009 | Byrum et al. |
| 7,510,530 B2 | 3/2009 | Hashimoto et al. |
| 7,530,943 B2 | 5/2009 | Lechner |
| 7,553,298 B2 | 6/2009 | Hunt et al. |
| 7,561,916 B2 | 7/2009 | Hunt et al. |
| 7,580,746 B2 | 8/2009 | Gilkerson et al. |
| 7,591,185 B1 | 9/2009 | Mothilal et al. |
| 7,593,777 B2 | 9/2009 | Gerber |
| 7,634,319 B2 | 12/2009 | Schneider et al. |
| 7,651,483 B2 | 1/2010 | Byrum et al. |
| 7,658,196 B2 | 2/2010 | Ferreri et al. |
| 7,699,770 B2 | 4/2010 | Hassler, Jr. et al. |
| 7,708,722 B2 | 5/2010 | Glenn |
| 7,762,998 B2 | 7/2010 | Birk et al. |
| 7,762,999 B2 | 7/2010 | Byrum |
| 7,775,215 B2 | 8/2010 | Hassler, Jr. et al. |
| 7,775,966 B2 | 8/2010 | Dlugos et al. |
| 7,811,275 B2 | 10/2010 | Birk et al. |
| 7,850,660 B2 | 12/2010 | Uth et al. |
| 7,862,546 B2 | 1/2011 | Conlon et al. |
| 7,909,754 B2 | 3/2011 | Hassler, Jr. et al. |
| 7,909,804 B2 | 3/2011 | Stats |
| 8,007,474 B2 | 8/2011 | Uth et al. |
| 8,480,560 B2 * | 7/2013 | Vendely .......... 600/37 |
| 2001/0052141 A1 | 12/2001 | Andersen |
| 2002/0013545 A1 | 1/2002 | Soltanpour et al. |
| 2002/0058969 A1 | 5/2002 | Noren et al. |
| 2002/0087147 A1 | 7/2002 | Hooper et al. |
| 2002/0095181 A1 | 7/2002 | Beyer |
| 2002/0139208 A1 | 10/2002 | Yatskov |
| 2002/0198548 A1 | 12/2002 | Robert |
| 2003/0045800 A1 | 3/2003 | Noren et al. |
| 2003/0045910 A1 | 3/2003 | Sorensen et al. |
| 2003/0073880 A1 | 4/2003 | Polsky et al. |
| 2003/0078506 A1 | 4/2003 | Noren et al. |
| 2003/0139690 A1 | 7/2003 | Aebli et al. |
| 2004/0064110 A1 | 4/2004 | Forsell |
| 2004/0065615 A1 | 4/2004 | Hooper et al. |
| 2004/0068233 A1 | 4/2004 | DiMatteo |
| 2004/0082908 A1 | 4/2004 | Whitehurst et al. |
| 2004/0111050 A1 | 6/2004 | Smedley et al. |
| 2004/0204692 A1 | 10/2004 | Eliasen |
| 2004/0254536 A1 | 12/2004 | Conlon et al. |
| 2004/0254537 A1 | 12/2004 | Conlon et al. |
| 2004/0260229 A1 | 12/2004 | Meir |
| 2004/0260319 A1 | 12/2004 | Egle |
| 2004/0267288 A1 | 12/2004 | Byrum et al. |
| 2004/0267291 A1 | 12/2004 | Byrum et al. |
| 2004/0267292 A1 | 12/2004 | Byrum et al. |
| 2004/0267293 A1 | 12/2004 | Byrum et al. |
| 2004/0267377 A1 | 12/2004 | Egle |
| 2005/0010177 A1 | 1/2005 | Tsai |
| 2005/0049578 A1 | 3/2005 | Tu et al. |
| 2005/0070875 A1 | 3/2005 | Kulessa |
| 2005/0070937 A1 | 3/2005 | Jambor et al. |
| 2005/0085778 A1 | 4/2005 | Parks |
| 2005/0092093 A1 | 5/2005 | Kang et al. |
| 2005/0131325 A1 | 6/2005 | Chen et al. |
| 2005/0131352 A1 | 6/2005 | Conlon et al. |
| 2005/0131383 A1 | 6/2005 | Chen et al. |
| 2005/0148956 A1 | 7/2005 | Conlon et al. |
| 2005/0149143 A1 | 7/2005 | Libbus et al. |
| 2005/0197636 A1 * | 9/2005 | Halili .......... 604/288.01 |
| 2005/0209573 A1 | 9/2005 | Brugger et al. |
| 2005/0240155 A1 | 10/2005 | Conlon |
| 2005/0240156 A1 | 10/2005 | Conlon |
| 2005/0267500 A1 | 12/2005 | Hassler, Jr. et al. |
| 2005/0277899 A1 | 12/2005 | Conlon et al. |
| 2005/0283041 A1 | 12/2005 | Egle |
| 2005/0283118 A1 | 12/2005 | Uth et al. |
| 2005/0283119 A1 | 12/2005 | Uth et al. |
| 2006/0074439 A1 | 4/2006 | Garner et al. |
| 2006/0122578 A1 | 6/2006 | Lord et al. |
| 2006/0161186 A1 | 7/2006 | Hassler, Jr. et al. |
| 2006/0173423 A1 | 8/2006 | Conlon |
| 2006/0173424 A1 | 8/2006 | Conlon |
| 2006/0178647 A1 | 8/2006 | Stats |
| 2006/0178648 A1 | 8/2006 | Barron et al. |
| 2006/0184141 A1 | 8/2006 | Smith et al. |
| 2006/0189887 A1 | 8/2006 | Hassler, Jr. et al. |
| 2006/0189888 A1 | 8/2006 | Hassler, Jr. et al. |
| 2006/0190039 A1 | 8/2006 | Birk et al. |
| 2006/0199997 A1 | 9/2006 | Hassler, Jr. et al. |
| 2006/0211912 A1 | 9/2006 | Dlugos et al. |
| 2006/0211913 A1 | 9/2006 | Dlugos et al. |
| 2006/0211914 A1 | 9/2006 | Hassler, Jr. et al. |
| 2006/0217668 A1 | 9/2006 | Schulze et al. |
| 2006/0217673 A1 | 9/2006 | Schulze et al. |
| 2006/0235445 A1 | 10/2006 | Birk et al. |
| 2006/0235448 A1 | 10/2006 | Roslin et al. |
| 2006/0247539 A1 | 11/2006 | Schugt et al. |
| 2006/0266128 A1 | 11/2006 | Clark et al. |
| 2006/0293625 A1 | 12/2006 | Hunt et al. |
| 2006/0293626 A1 | 12/2006 | Byrum et al. |
| 2006/0293627 A1 | 12/2006 | Byrum et al. |
| 2006/0293628 A1 | 12/2006 | Hunt et al. |
| 2007/0010790 A1 | 1/2007 | Byrum et al. |
| 2007/0015954 A1 | 1/2007 | Dlugos |
| 2007/0015955 A1 | 1/2007 | Tsonton |
| 2007/0016231 A1 | 1/2007 | Jambor et al. |
| 2007/0027356 A1 | 2/2007 | Ortiz |
| 2007/0038255 A1 | 2/2007 | Kieval et al. |
| 2007/0049877 A1 * | 3/2007 | Patton .......... 604/288.01 |
| 2007/0060959 A1 | 3/2007 | Salo et al. |
| 2007/0073250 A1 | 3/2007 | Schneiter |

(56) References Cited

U.S. PATENT DOCUMENTS

| | | |
|---|---|---|
| 2007/0078391 A1 | 4/2007 | Wortley et al. |
| 2007/0088336 A1 | 4/2007 | Dalton |
| 2007/0088391 A1 | 4/2007 | McAlexander et al. |
| 2007/0129765 A1 | 6/2007 | Gilkerson et al. |
| 2007/0135758 A1 | 6/2007 | Childers et al. |
| 2007/0149947 A1 | 6/2007 | Byrum |
| 2007/0156013 A1 | 7/2007 | Birk |
| 2007/0158769 A1 | 7/2007 | You |
| 2007/0161958 A1 | 7/2007 | Glenn |
| 2007/0167672 A1 | 7/2007 | Dlugos et al. |
| 2007/0173685 A1 | 7/2007 | Jambor et al. |
| 2007/0185462 A1 | 8/2007 | Byrum |
| 2007/0191717 A1 | 8/2007 | Rosen et al. |
| 2007/0205384 A1 | 9/2007 | Kurosawa |
| 2007/0208313 A1 | 9/2007 | Conlon et al. |
| 2007/0213837 A1 | 9/2007 | Ferreri et al. |
| 2007/0219510 A1 | 9/2007 | Zinn et al. |
| 2007/0235083 A1 | 10/2007 | Dlugos |
| 2007/0250086 A1 | 10/2007 | Wiley et al. |
| 2007/0255165 A1 | 11/2007 | Uesugi et al. |
| 2007/0255234 A1 | 11/2007 | Haase et al. |
| 2007/0265666 A1 | 11/2007 | Roberts et al. |
| 2007/0282196 A1 | 12/2007 | Birk et al. |
| 2007/0293829 A1 | 12/2007 | Conlon et al. |
| 2008/0009680 A1 | 1/2008 | Hassler, Jr. |
| 2008/0015406 A1 | 1/2008 | Dlugos et al. |
| 2008/0039772 A1 | 2/2008 | Chantriaux et al. |
| 2008/0058632 A1 | 3/2008 | Tai et al. |
| 2008/0097496 A1 | 4/2008 | Chang et al. |
| 2008/0114308 A1 | 5/2008 | di Palma et al. |
| 2008/0119798 A1 | 5/2008 | Chantriaux et al. |
| 2008/0243093 A1 | 10/2008 | Kalpin et al. |
| 2008/0249806 A1 | 10/2008 | Dlugos et al. |
| 2008/0250340 A1 | 10/2008 | Dlugos et al. |
| 2008/0250341 A1 | 10/2008 | Dlugos et al. |
| 2008/0255403 A1 | 10/2008 | Voegele et al. |
| 2008/0255414 A1 | 10/2008 | Voegele et al. |
| 2008/0255425 A1 | 10/2008 | Voegele et al. |
| 2008/0255459 A1 | 10/2008 | Voegele et al. |
| 2008/0255537 A1 | 10/2008 | Voegele et al. |
| 2008/0281412 A1 | 11/2008 | Smith et al. |
| 2008/0287969 A1 | 11/2008 | Tsonton et al. |
| 2008/0287974 A1 | 11/2008 | Widenhouse et al. |
| 2008/0312553 A1 | 12/2008 | Timmons |
| 2008/0319435 A1 | 12/2008 | Rioux et al. |
| 2009/0018608 A1 | 1/2009 | Schwartz et al. |
| 2009/0048524 A1 | 2/2009 | Wildau et al. |
| 2009/0054914 A1 | 2/2009 | Lechner |
| 2009/0062825 A1 | 3/2009 | Pool et al. |
| 2009/0071258 A1 | 3/2009 | Kouda et al. |
| 2009/0076466 A1 | 3/2009 | Quebbemann et al. |
| 2009/0082757 A1 | 3/2009 | Rogers et al. |
| 2009/0082793 A1 | 3/2009 | Birk |
| 2009/0093768 A1 | 4/2009 | Conlon et al. |
| 2009/0099538 A1 | 4/2009 | Paganon |
| 2009/0105735 A1 | 4/2009 | Stam et al. |
| 2009/0112308 A1 | 4/2009 | Kassem |
| 2009/0118572 A1 | 5/2009 | Lechner |
| 2009/0149874 A1 | 6/2009 | Ortiz et al. |
| 2009/0157106 A1 | 6/2009 | Marcotte et al. |
| 2009/0157107 A1 | 6/2009 | Kierath et al. |
| 2009/0157113 A1 | 6/2009 | Marcotte et al. |
| 2009/0171375 A1 | 7/2009 | Coe et al. |
| 2009/0171378 A1 | 7/2009 | Coe et al. |
| 2009/0171379 A1 | 7/2009 | Coe et al. |
| 2009/0192404 A1 | 7/2009 | Ortiz et al. |
| 2009/0192415 A1 | 7/2009 | Ortiz et al. |
| 2009/0192533 A1 | 7/2009 | Dlugos, Jr. et al. |
| 2009/0192534 A1 | 7/2009 | Ortiz et al. |
| 2009/0192541 A1 | 7/2009 | Ortiz et al. |
| 2009/0198261 A1 | 8/2009 | Schweikert |
| 2009/0202387 A1 | 8/2009 | Dlugos, Jr. et al. |
| 2009/0204131 A1 | 8/2009 | Ortiz et al. |
| 2009/0204132 A1 | 8/2009 | Ortiz et al. |
| 2009/0209995 A1 | 8/2009 | Byrum et al. |
| 2009/0216255 A1 | 8/2009 | Coe et al. |
| 2009/0221974 A1 | 9/2009 | Paganon |
| 2009/0222031 A1 | 9/2009 | Axelsson |
| 2009/0222065 A1 | 9/2009 | Dlugos, Jr. et al. |
| 2009/0227862 A1 | 9/2009 | Smith et al. |
| 2009/0228028 A1 | 9/2009 | Coe et al. |
| 2009/0228072 A1 | 9/2009 | Coe et al. |
| 2009/0248125 A1 | 10/2009 | Brostrom |
| 2009/0248126 A1 | 10/2009 | Nippoldt et al. |
| 2009/0254052 A1 | 10/2009 | Birk et al. |
| 2009/0259190 A1 | 10/2009 | Birk et al. |
| 2009/0259191 A1 | 10/2009 | Birk et al. |
| 2009/0259231 A1 | 10/2009 | Birk et al. |
| 2009/0264901 A1 | 10/2009 | Franklin et al. |
| 2009/0270904 A1 | 10/2009 | Birk et al. |
| 2009/0299216 A1 | 12/2009 | Chen et al. |
| 2009/0299672 A1 | 12/2009 | Zhang et al. |
| 2009/0306462 A1 | 12/2009 | Lechner |
| 2009/0308169 A1 | 12/2009 | Mothilal et al. |
| 2010/0087843 A1 | 4/2010 | Bertolote et al. |
| 2010/0100079 A1 | 4/2010 | Berkcan et al. |
| 2010/0114149 A1 | 5/2010 | Albrecht et al. |
| 2010/0130941 A1 | 5/2010 | Conlon et al. |
| 2010/0152532 A1 | 6/2010 | Marcotte |
| 2010/0191271 A1 | 7/2010 | Lau et al. |
| 2010/0211085 A1 | 8/2010 | Uth et al. |
| 2010/0217198 A1 | 8/2010 | Franklin et al. |
| 2010/0217199 A1 | 8/2010 | Uth et al. |
| 2010/0217200 A1 | 8/2010 | Uth et al. |
| 2010/0228080 A1 | 9/2010 | Tavori et al. |
| 2010/0234808 A1 | 9/2010 | Uth et al. |
| 2011/0054407 A1 | 3/2011 | Olroyd et al. |
| 2011/0082426 A1 | 4/2011 | Conlon et al. |

FOREIGN PATENT DOCUMENTS

| | | |
|---|---|---|
| DE | 3927001 | 2/1991 |
| DE | 4211045 | 10/1993 |
| DE | 4423706 | 2/1996 |
| DE | 19751791 | 5/1997 |
| DE | 19745654 | 4/1999 |
| EP | 0343910 | 11/1989 |
| EP | 0611561 | 9/1993 |
| EP | 0858814 | 8/1998 |
| EP | 0867197 | 9/1998 |
| EP | 1057457 | 12/2000 |
| EP | 1205211 | 5/2002 |
| EP | 1346753 | 9/2003 |
| EP | 1396242 | 3/2004 |
| EP | 1396243 | 3/2004 |
| EP | 1488824 | 12/2004 |
| EP | 1543861 | 6/2005 |
| EP | 1547643 | 6/2005 |
| EP | 1591140 | 11/2005 |
| EP | 1629862 | 3/2006 |
| EP | 1736194 | 12/2006 |
| EP | 1736195 | 12/2006 |
| EP | 1736196 | 12/2006 |
| EP | 1736197 | 12/2006 |
| EP | 1736198 | 12/2006 |
| EP | 1736199 | 12/2006 |
| EP | 1870126 | 12/2007 |
| EP | 1985263 | 10/2008 |
| EP | 2070494 | 6/2009 |
| EP | 2095798 | 9/2009 |
| FR | 2740977 | 5/1997 |
| FR | 2797181 | 2/2001 |
| FR | 2823663 | 10/2002 |
| FR | 2851168 | 8/2004 |
| FR | 2855744 | 12/2004 |
| FR | 2916980 | 12/2008 |
| JP | 2119877 | 5/1990 |
| JP | 8107934 | 4/1996 |
| SU | 1823791 | 6/1991 |
| WO | WO 92/20519 | 11/1992 |
| WO | WO 94/22520 | 10/1994 |
| WO | WO 96/40357 | 12/1996 |
| WO | WO 97/01370 | 1/1997 |
| WO | WO 99/20338 | 4/1999 |

(56) References Cited

FOREIGN PATENT DOCUMENTS

| WO | WO 99/26543 | 6/1999 |
|----|-------------|--------|
| WO | WO 99/34859 | 7/1999 |
| WO | WO 00/15158 | 3/2000 |
| WO | WO 00/33901 | 6/2000 |
| WO | WO 01/10359 | 2/2001 |
| WO | WO 01/49245 | 7/2001 |
| WO | WO 01/80926 | 11/2001 |
| WO | WO 01/95813 | 12/2001 |
| WO | WO 02/10667 | 2/2002 |
| WO | WO 02/074381 | 9/2002 |
| WO | WO 03/105732 | 12/2003 |
| WO | WO 2004/016971 | 3/2004 |
| WO | WO 2005/037055 | 4/2005 |
| WO | WO 2005/072627 | 8/2005 |
| WO | WO 2006/021695 | 3/2006 |
| WO | WO 2009/007526 | 1/2009 |
| WO | WO 2009/129474 | 10/2009 |

OTHER PUBLICATIONS

Helioscopie Product Insert for Heliogast, pp. 1-11 (undated).
Autumn K. et al.; "Evidence of Van Der Waals Adhesion in Gecko Setae"; PNAS; vol. 99; No. 19; pp. 12252-12256; Sep. 17, 2012.
Geim AK. et al.; "Microfabricated Adhesive Mimicking Gecko Foot-Hair"; Nature Materials Abstract only; vol. 2; No. 7; 2003.
Yamagami, Takuji; "Technical Developments: Use of Targeting Guide Wire in Left Subclavian Puncture During Percutaneous Implantation of Port-Catheter Systems Using the Catheter Tip Fixation Method" European Radiology; vol. 13; pp. 863-866; 2003.
Yurdumakan B., et al.; "Synthetic Gecko Foot-Hairs from Multiwalled Carbon Nanotubes"; The Royal Society of Chemistry; p. 3799-3801; 2005.

* cited by examiner

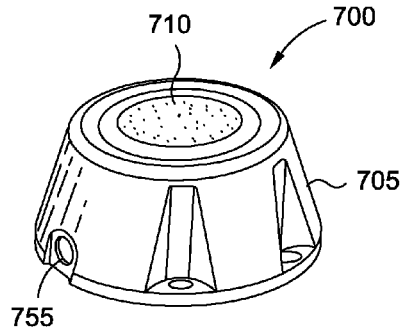
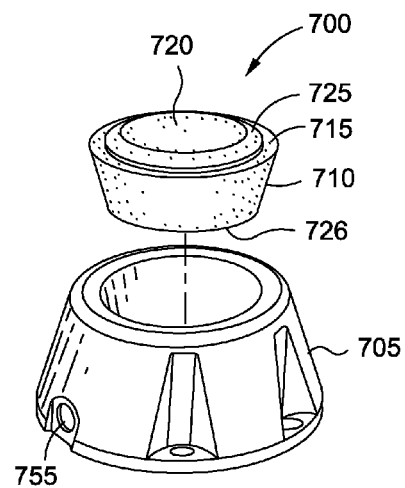
FIG. 7A  FIG. 7B
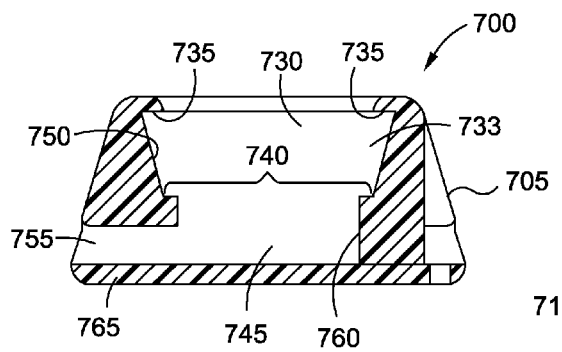
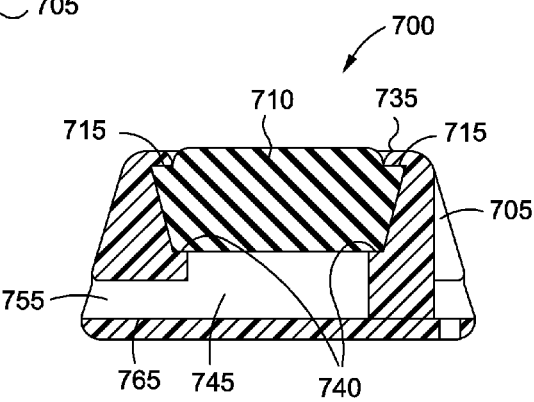
FIG. 7C
FIG. 7D
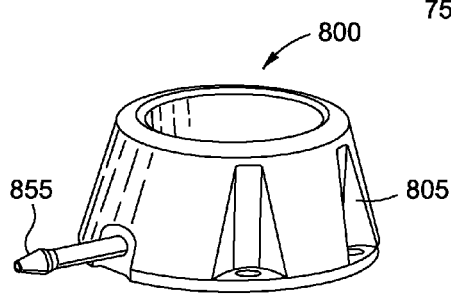
FIG. 8

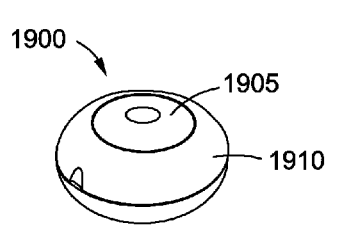
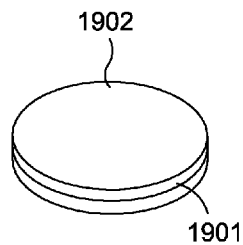
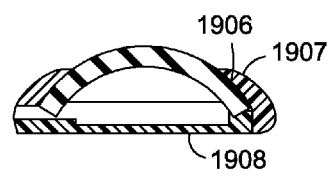
FIG. 19A  FIG. 19B  FIG. 19C
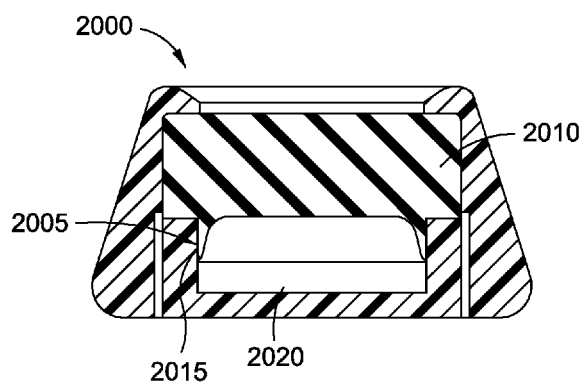
FIG. 20
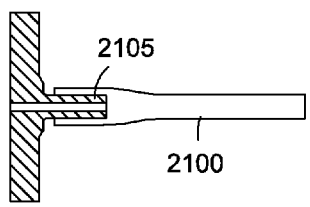
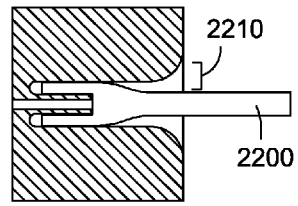
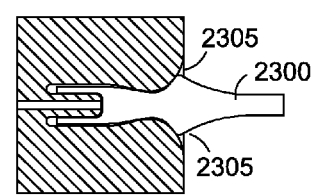
FIG. 21  FIG. 22  FIG. 23

IMPLANTABLE INJECTION PORT

FIELD

The present invention generally relates to medical systems and apparatus and uses thereof for treating obesity and/or obesity-related diseases. More specifically, the present invention relates to injection ports penetrable by a needle to add or remove saline and/or other appropriate fill materials to a gastric banding system.

BACKGROUND

Adjustable gastric banding apparatus have provided an effective and substantially less invasive alternative to gastric bypass surgery and other conventional surgical weight loss procedures. Despite the positive outcomes of invasive weight loss procedures, such as gastric bypass surgery, it has been recognized that sustained weight loss can be achieved through a laparoscopically-placed gastric band, for example, the LAP-BAND® (Allergan, Inc., Irvine, Calif.) gastric band or the LAP-BAND AP® (Allergan, Inc., Irvine, Calif.) gastric band. Generally, gastric bands are placed about the fundus, or cardia, or esophageal junction, of a patient's upper stomach forming a stoma that restricts food's passage into a lower portion of the stomach. When the stoma is of an appropriate size that is restricted by a gastric band, the food held in the upper portion of the stomach may provide a feeling of satiety or fullness that discourages overeating. Unlike gastric bypass procedures, gastric band apparatus are reversible and require no permanent modification to the gastrointestinal tract. An example of a gastric banding system is disclosed in Roslin, et al., U.S. Patent Pub. No. 2006/0235448, the entire disclosure of which is incorporated herein by this specific reference.

Existing gastric bands periodically require adjustments to maintain an effective constriction about the stomach, to account for changes in the stomach tissue, reduction of fat or other factors causing movement and/or size change of the stomach. Some attempts have been made to allow for such adjustment of gastric bands. For example, hydraulic gastric bands utilize a fluid such as saline to fill an inflatable portion of the gastric band using a subcutaneous injection port. Adjustments to the amount of inflation may be made by injecting or extracting the fluid through the patient's skin into or out of the injection port, which then directs the fluid into or out of the inflatable portion of the gastric band.

Current injection ports are typically designed to include complicated and/or intricate solid compressing geometries which may reduce functional performance and/or increase cost.

For example, with reference to FIGS. 1A and 1B, Redmond, et al., U.S. Pat. No. 4,781,680, discloses an injection port having a plurality of inter-related components including a filter element and a cup-shaped compression member, among other components.

With reference to FIG. 2, Johnston, et al., U.S. Pat. No. 4,886,501 discloses a low-acute angle implantable device having a septum axially aligned with a connector.

With reference to FIG. 3, Fogarty, et al., U.S. Pat. No. 6,039,712, discloses an implantable injection port having multiple elastomeric penetrable layers and mesh layers. The mesh layers are for creating fluid channels for the passage of fluids to the tubing port/connector.

Accordingly, in certain embodiments, it may be desirable to develop an injection port being of a simpler assembly, improved reliability, cost savings, needle accessibility and/or sealing functionality of the device, among other benefits.

SUMMARY

Generally described herein are certain embodiments directed to an injection port fluidly coupled to a gastric banding system, the injection port for simplifying the port-targeting process when a medical professional attempts to penetrate the injection port with a needle during a gastric band-adjusting procedure.

In one embodiment, provided is an injection port for use with a gastric band for the treatment of obesity. The injection port is implantable in a patient and fluidly coupled to tubing connected to an inflatable portion of a gastric band, which may comprise a septum having a top surface, a bottom surface, and a side wall, the side wall of the septum connecting the top and bottom surfaces. The gastric band also may include a housing configured to receive and secure the septum, the housing further including a first inner side wall configured to taper inwards such that an opening defined at a first end is larger than an opening defined at a second end, a second inner side wall having a first end and a second end, the first end of the second inner wall joined to the second end of the first inner side wall, a bottom surface joined to the second end of the second inner wall, and wherein the first inner side wall, the second inner side wall and the bottom surface defining a cavity having at least two portions, a first portion of the cavity defined by the first inner side wall and for receiving the septum and allowing the first inner side wall to secure the septum by axially exerting compression on the septum, and a second portion of the cavity defined by the second inner side wall and the bottom surface, the second portion of the cavity for holding fluid, and a retaining lip joined to the first inner side wall, and for securing the top surface of the septum, the housing configured to secure the bottom surface of the septum via the tapering of the first inner side wall.

In one embodiment, provided is a method of manufacturing an access port for use with a gastric band for the treatment of obesity. The method comprises: molding a housing having a cavity defined by a side wall having a tapered segment and a bottom wall; molding a septum configured to fit within the cavity of the housing, the molding further configured to have a tapering substantially the same as a portion of the tapered segment; pressing the septum into the cavity of the housing via a horn having geometric mold for a formation of a retaining lip; and melting a top edge of the housing into the geometric mold of the horn to form the retaining lip on the septum while the septum is pressed into the cavity of the housing.

In one embodiment, provided is an injection port implantable in a patient for use with a gastric band for the treatment of obesity and fluidly coupled to a tubing (or a tube) connected to an inflatable portion of the gastric band. The injection port comprising: a needle penetrable septum having a needle-entry surface, a sealing surface, a retention ring, and a bottom surface, the retention ring positioned between the needle-entry surface and the bottom surface; a housing including a retention lip defining a top retaining surface for overhanging and contacting the retention ring to prevent the septum from exiting the housing when the septum is pressed into the housing, a first side wall joined to the retention lip for defining a cavity for receiving the septum, the first side wall for guiding the septum when the septum is pressed into the cavity, a retention protrusion joined to the first side wall, and defining a bottom retaining surface for contacting a bottom surface of the septum and preventing the contacted portions of the bottom surface of the septum from extending beyond the retention protrusion when the retention lip is overhanging and contacting the retention ring of the septum, and a second side wall joined to the retention protrusion, the second side wall for defining a fluid reservoir for receiving fluid from or passing fluid to the inflatable portion of the gastric band.

In one embodiment, provided is an injection port implantable in a patient for use with a gastric band for the treatment of obesity and fluidly coupled to tubing connected to an inflatable portion of the gastric band. The injection port comprising: a septum sized to have a first diameter and having a needle-entry surface, a bottom surface and a side wall configured to attach the needle-entry surface to the bottom surface; a hemispherically-shaped housing including: a retaining ring defining a first portion of a cavity having a diameter equal to the first diameter to receive the septum, and a hemispherically-shaped bottom wall defining a second portion of the cavity for receiving fluid from or passing fluid to the inflatable portion of the gastric band, the second portion of the cavity having a second diameter of an incrementally decreasing size moving away from the retaining ring; and a covering seal having a ring portion configured to fit on the outside of retaining ring, and further configured to secure the septum inside the first portion of the cavity.

In one embodiment, provided is a method of manufacturing an injection port for use with a gastric band for the treatment of obesity. The method comprising: molding a housing including an opening at a top of the housing leading into a cavity defined by an inner side wall of the housing and an inner bottom wall of the housing, the cavity having a first portion and a second portion, the first portion of the cavity being positioned between the opening and the second portion of the cavity; increasing the diameter of the first portion of the cavity; adding silicone into the first portion of the cavity after increasing the diameter of the first portion of the cavity to form a septum; molding the septum under compression; and decreasing the diameter of the first portion of the cavity after molding the septum under compression.

In one embodiment, provided is an injection port molding system for manufacturing an injection port for use with a gastric band for the treatment of obesity. The system comprising: a septum having a top surface, a bottom surface and a side wall for joining the top surface and the bottom surface; a compression ring configured to receive the septum and further defining a reservoir including: a ring portion for holding the septum, and a reservoir defining portion integrated with the ring portion, the reservoir defining portion having a connector interface; a stem insert having a first end inserted into the connector interface, and a second end leading away from the compression ring; a molding device for allowing the injection of a solid material to define a housing and encapsulating at least a portion of the septum, the compression ring and the stem insert, the molding device including: a top mold having a cut-out portion for positioning of the septum, the compression ring and the stem insert, and a bottom mold for fitting the top mold and to hold the septum, the reservoir and the stem insert in position.

In one embodiment, provided is a method of manufacturing an injection port for use with a gastric band for the treatment of obesity. The method comprising: molding a housing including an opening at a top of the housing leading into a cavity defined by an inner side wall of the housing and an inner bottom wall of the housing, the cavity having a first portion and a second portion, the first portion of the cavity being position between the opening and the second portion of the cavity; inserting a septum into the first portion of the cavity leaving a gap between an exterior of the septum and the inner side wall; and increasing radial compression exerted on the septum by adding liquid silicone to fill the gap between the exterior of the septum and the inner side wall of the housing.

In one embodiment, provided is a method of manufacturing a pre-compressed septum having a compression ring and a septum portion for usage in an injection port. The method comprising: curing a silicone material resulting in the septum; and surrounding the septum with the compression ring by stretching the compression ring about the exterior of the septum or by injection molding the compression ring about the exterior of the septum.

In one embodiment, provided is an injection port dome assembly for use with a gastric band for the treatment of obesity. The injection port dome assembly comprising: a housing having a substantially circular cut-out portion, the housing including: a circumferential edge defining the cut-out portion, the cut-out portion having a diameter, a bottom surface having a diameter larger than the diameter of the cut-out portion, and a curved side wall extending from the circumferential edge to the bottom surface; a compressed silicone membrane configured to fill the cut-out portion such that the housing and the silicone member substantially forms a hemispherically-shaped object; a mesh layer integrated on an exterior surface of the compressed silicone membrane.

In one embodiment, provided is a gastric banding system for the treatment of obesity in a patient, the gastric banding system including: a gastric band having an inflatable portion configured to be disposed about a stomach of the patient; an access port coupled to the gastric band for the addition or removal of fluid in the gastric band to adjust the degree of constriction that the gastric band imparts on the stomach of the patient; and a tubing having a first end connected to the gastric band and a second end connected to the access port, wherein the tubing is connected to the access port via a sunken connector, the sunken connector including: a first portion located within a housing of the access port, and a second portion located outside of the housing of the access port.

In one embodiment, provided is a gastric band that is positioned about a patient's stomach for the treatment of obesity. The gastric band comprising: an inflatable portion disposable about a stomach of the patient; an injection port fluidly coupled to the inflatable portion tubing to fill and drain the inflatable portion; a tubing having a first end for connecting to the inflatable portion and a second end for connecting to the inflatable portion, the tubing for carrying fluid from the injection port to the inflatable portion to fill the inflatable portion, and for carrying fluid from the inflatable portion to the injection port to drain the inflatable portion; and an integrated ring attached to an exterior surface of the tubing, the integrated ring defines at least one hole allowing in-growth of bodily tissue within the hole to integrate the bodily tissue and the integrated ring.

BRIEF DESCRIPTION OF THE DRAWINGS

The features, obstacles, and advantages of the present invention will become more apparent from the detailed description set forth below when taken in conjunction with the drawings, wherein:

FIG. 7A illustrates a perspective view of an injection port according to an embodiment of the present invention;

FIG. 7B illustrates a perspective view of the injection port of FIG. 7A with the septum in a removed position according to an embodiment of the present invention;

FIG. 7C illustrates a perspective, cross-sectional view of the injection port of FIG. 7A without a septum according to an embodiment of the present invention;

FIG. 7D illustrates a perspective, cross-sectional view of the injection port of FIG. 7A according to an embodiment of the present invention;

FIG. 8 illustrates a perspective view of an access port without a septum according to an embodiment of the present invention;

FIG. 19A illustrates a perspective view of a dome-shaped access port according to an embodiment of the present invention;

FIG. 19B illustrates a septum material for use in the construction of the dome-shaped access port of FIG. 19A according to an embodiment of the present invention;

FIG. 19C illustrates a cross-sectional view of the dome-shaped access port of FIG. 22A according to an embodiment of the present invention;

FIG. 20 illustrates a cross-sectional view of an access port with a lip seal according to an embodiment of the present invention;

FIG. 21 illustrates a prior art stem connector;

FIG. 22 illustrates a stem connector according to an embodiment of the present invention;

FIG. 23 illustrates a stem connector according to an embodiment of the present invention.

DETAILED DESCRIPTION

Apparatus, systems and/or methods that implement the embodiments of the various features of the present invention will now be described with reference to the drawings. The drawings and the associated descriptions are provided to illustrate some embodiments of the present invention and not to limit the scope of the present invention. Throughout the drawings, reference numbers are re-used to indicate correspondence between referenced elements.

The present invention generally provides injection port designs and improvements thereof which allow, for example, cheaper injection ports for gastric banding systems while still maintaining acceptable levels of reliability and functionality. These injection ports allow a physician to connect to the closed fluid system of the gastric banding system. In essence, the physician may locate the position of the injection port, puncture the patient's skin and the septum of the injection port with a needle, and make the necessary fluid adjustment to the gastric banding system by either adding or removing the fluid. Once completed, the needle is withdrawn from the septum and the patient's skin and the septum self-seals the puncture of the injection port.

While discussed herein to be related to a gastric banding system, one skilled in the art will understand that the present invention is versatile and may be implemented with respect to any medical system, gastric-band related or not, which may be enhanced with an injection port. For example, cancer patients who require an injection port for frequent access to their veins may benefit from the implementation of an embodiment of an injection port described herein.

Figure 1:
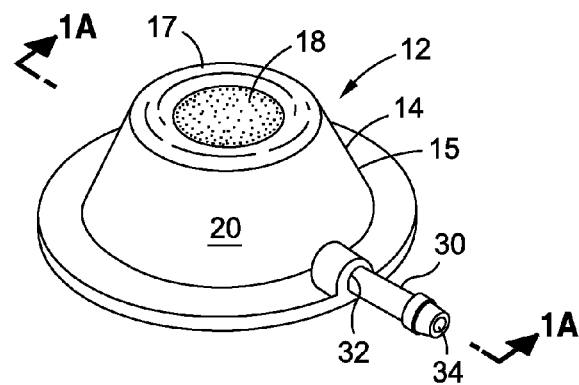
FIG. 1 illustrates a prior art injection port.
Figure 1A:
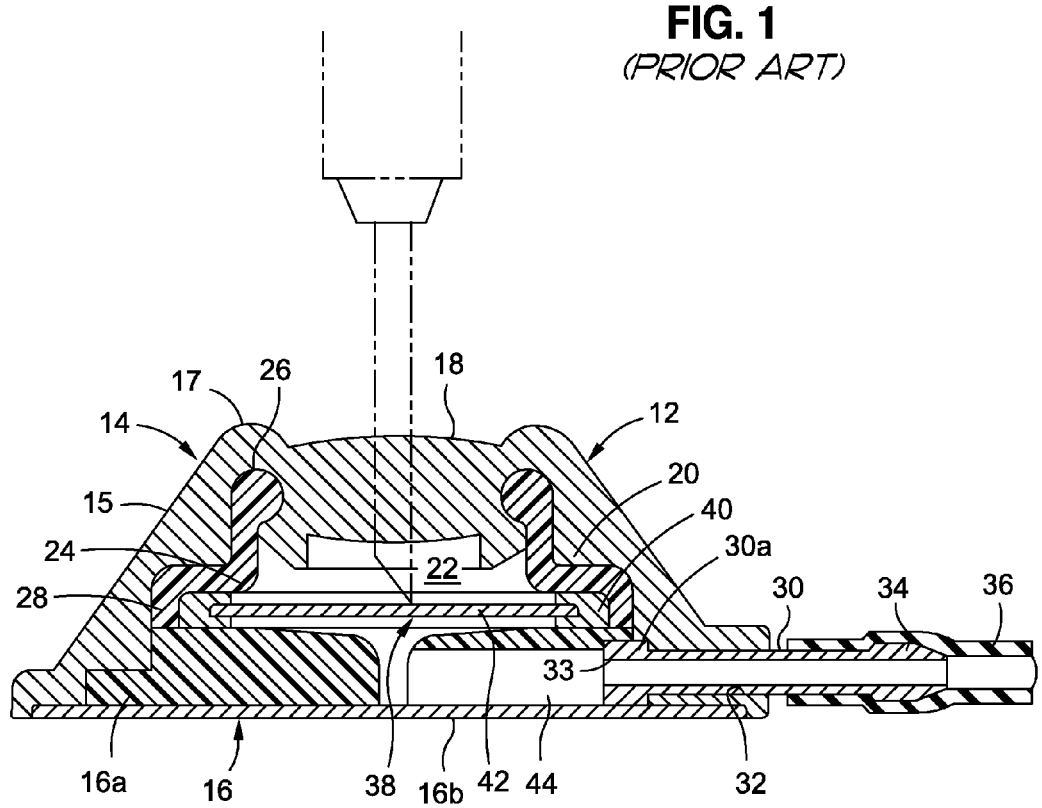
FIG. 1A illustrates a prior art injection port.
Figure 2:
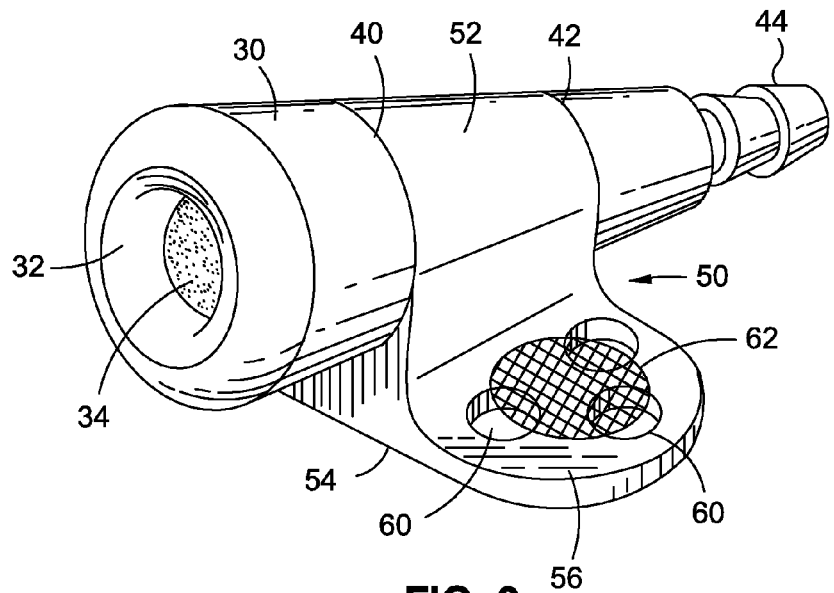
FIG. 2 illustrates a prior art injection port having a septum axially aligned with a connector.
Figure 3:
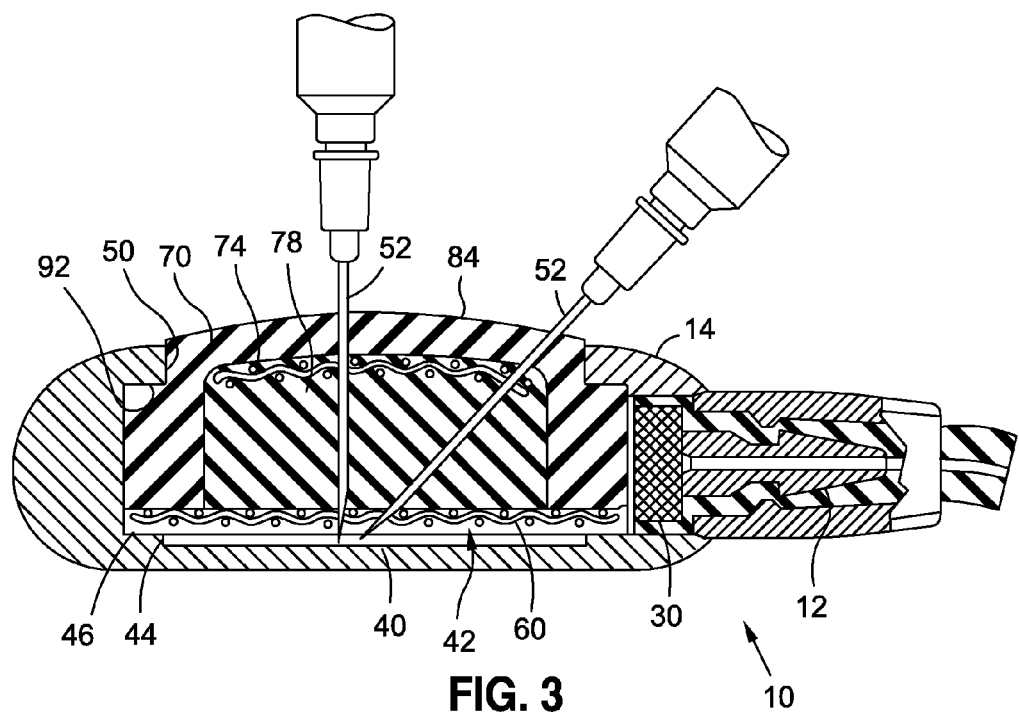
FIG. 3 illustrates a prior art injection port having multiple elastomeric penetrable layers and mesh layers.
Figure 4:
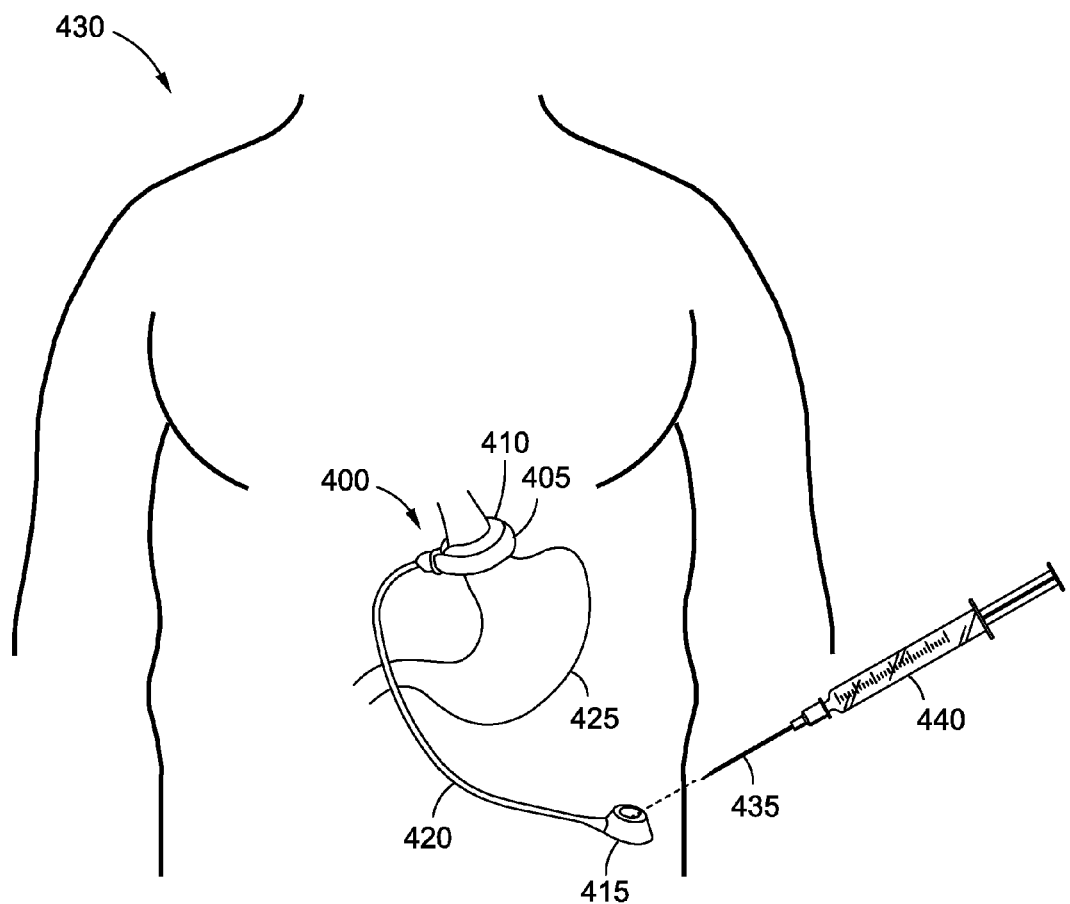
FIG. 4 illustrates an implanted gastric banding system according to an embodiment of the present invention.

Turning to FIG. 4, an implanted gastric banding system 400 is illustrated as implanted within a patient's body 430, and more specifically, forming a stoma around an upper portion of the stomach 425 of the patient's body 430. The implanted gastric banding system 400 may include a gastric band 405 having an inflatable portion 410. The gastric band 405 may be fluidly coupled with an injection port or an access port 415 via a tube or tubing 420. As used herein, the terms "injection port" and "access port" may be interchangeable. A syringe 440 having a needle 435 may penetrate the body 430 of the patient at a location proximal to the injection port 415 to add or remove fluid. The fluid added or removed may either inflate (if fluid is added) or deflate (if fluid is removed) the inflatable portion 410 of the gastric band 405, thereby increasing (if fluid is added) the degree of constriction that the gastric band 405 imparts on the upper portion of the stomach 425 or decreasing (if fluid is removed) the degree of constriction that the gastric band 405 imparts on the upper stomach 425. In this manner, adjustments to the gastric banding system 400 may be performed via the injection port 415.

Figure 5A:
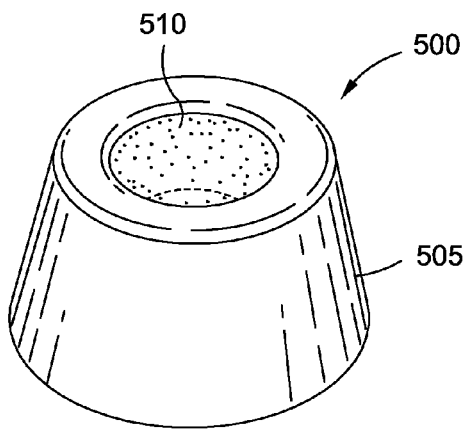
FIG. 5A illustrates a perspective view of an injection port according to an embodiment of the present invention.

FIG. 5A illustrates a staked-septum injection port 500. For clarity, a stem or a tubing-insertion access is not shown. In one embodiment, the injection port 500 may be injection port 415 of FIG. 4. The injection port 500 may include a housing 505 and an inserted septum 510.

Figure 5B:
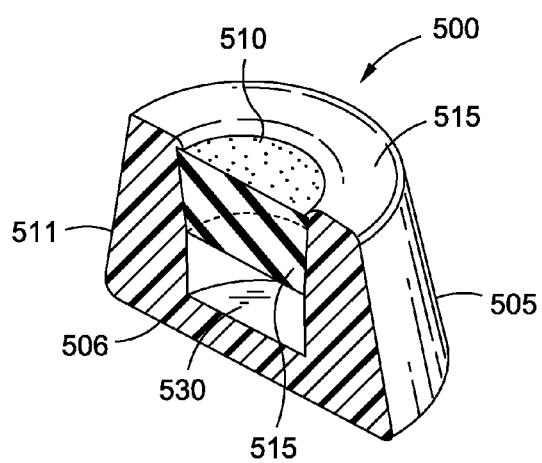
FIG. 5B illustrates a perspective, cross-sectional view of the injection port of FIG. 5A according to an embodiment of the present invention.

FIG. 5B illustrates a cross-sectional view of the injection port 500 of FIG. 5A. In this view, a structure of a retaining lip 515 is visible and shown to overhang the outside or needle-injection surface of the injection port 500. The retaining lip 515 may serve to prevent the septum 510 from moving out of the housing 505. The geometry of the housing 505 further prevents the septum 510 from moving deeper into the housing 505, when the septum 510 is pressed into position. For example, a diameter 511 of the bottom surface of the septum 510 may be greater than a diameter 506 of the bottom cavity 530 of the housing 505. In other words, since the diameter 511 of the septum 510 is greater than a diameter of the bottom cavity 530, the septum 510 is prevented from further movement into the bottom cavity 530. In this manner, the septum 510 may be securely held in place or position after being pressed into the housing 505.

In one embodiment, when the septum 510 is held in position within the housing 505, the retaining lip 515 and/or the tight fit of the septum 510 within the housing 505 may cause axial and/or radial compression, thereby enhancing a self-sealing feature of the septum 510 in addition to holding the septum 510 in place.

Figure 5C:
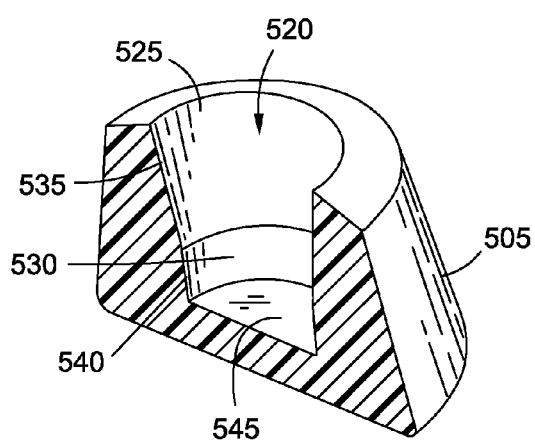
FIG. 5C illustrates a perspective, cross-sectional view of the injection port of FIG. 5A without the septum according to an embodiment of the present invention.

FIG. 5C illustrates the housing 505 without the septum 510 for further clarity of the structural components of the housing 505. As shown, the housing 505 may include a cavity 520, which may be divided into two portions, a top cavity 525 and a bottom cavity 530. The top cavity 525 may be defined by a side inner wall 535 spanning circumferentially about an interior portion of the housing 505. The side inner wall 535 may also taper inwards moving away from an opening of the cavity 520. The top cavity 525 may be configured to have a similar shape and/or dimensions as the septum 510 in order to house the septum 510. The bottom cavity 530 may be defined by a second inner side wall 540 and a bottom surface 545 of the housing 505. The bottom cavity 530 may be intended to act as a fluid reservoir for carrying fluid injected by a needle to the inflatable portion of a gastric band and/or for carrying fluid from the inflatable portion of the gastric band to the needle.

Figure 5D:
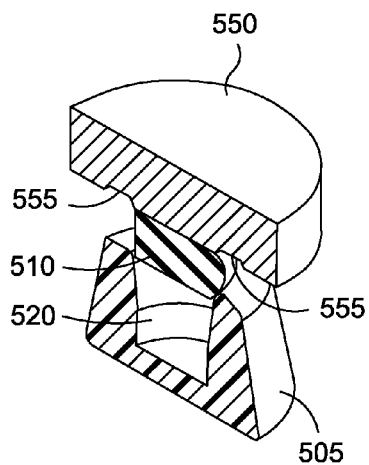
FIG. 5D illustrates a perspective, cross-sectional view of the injection port of FIG. 5A during a manufacturing process according to an embodiment of the present invention.
Figure 5E:
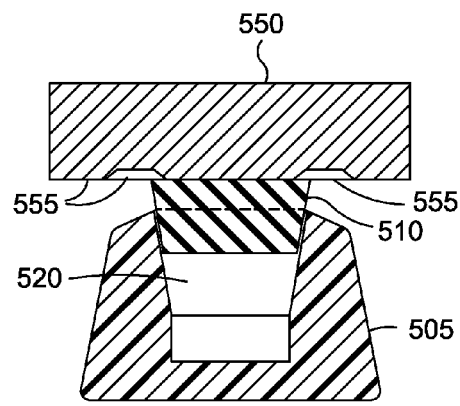
FIG. 5E illustrates a cross-sectional view of the injection port of FIG. 5A during a manufacturing process according to an embodiment of the present invention.

FIG. 5D and FIG. 5E illustrate a perspective, cross-sectional view and a cross-sectional view, respectively, of a septum insertion and sealing process of the injection port 500. As shown, a horn 550, which acts as an insertion and sealing tool, may be initially positioned above the septum 510. The horn 550 may include a lip mold 555 located on a surface of the horn 550 adjacent to the portion of the horn 550 attached to the septum 510. The lip mold 555 may surround an outer circumference of the septum 510. As shown, the horn 550 may direct and position the septum 510 to be pressed into the top cavity 525.

Figure 5F:
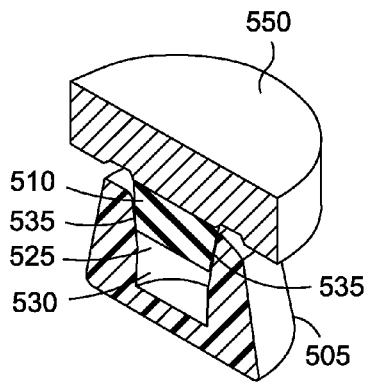
FIG. 5F illustrates a perspective, cross-sectional view of the injection port of FIG. 5A during a manufacturing process according to an embodiment of the present invention.
Figure 5G:
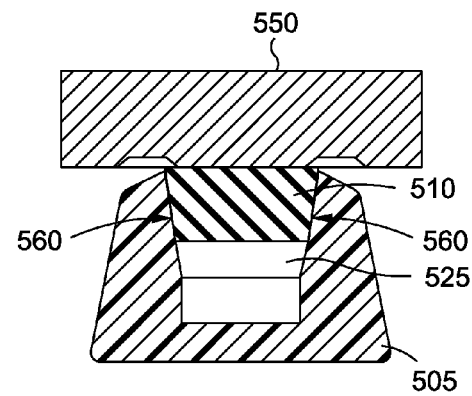
FIG. 5G illustrates a cross-sectional view of the injection port of FIG. 5A during a manufacturing process according to an embodiment of the present invention.

FIG. 5F and FIG. 5G further illustrate a perspective, cross-sectional view and a cross-sectional view, respectively, of a pressing step of the septum insertion and sealing process of the injection port 500. Here, the horn 550 is being pressed downward to move the septum 510 into the top cavity 525 of the housing 505. In this position, the first inner side wall 535 may be in contact with the septum 510 and may exert radial compression on the septum 510. As the septum 510 moves lower into the housing 510, radial forces may be increased due to the tapering of the inner side wall 535, thereby increasing compression on the septum 510.

Figure 5H:
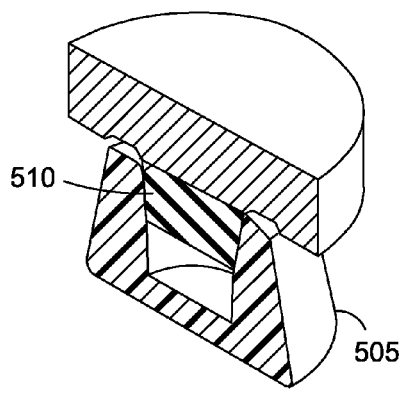
FIG. 5H illustrates a perspective, cross-sectional view of the injection port of FIG. 5A during a manufacturing process according to an embodiment of the present invention.
Figure 5I:
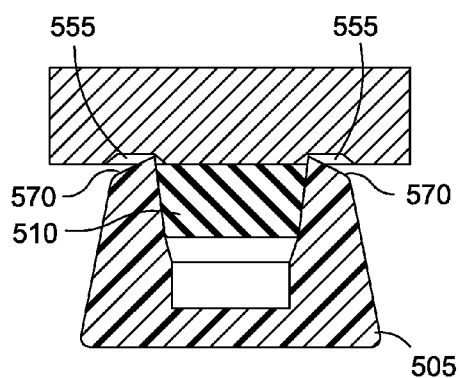
FIG. 5I illustrates a cross-sectional view of the injection port of FIG. 5A during a manufacturing process according to an embodiment of the present invention.

FIGS. 5H and 5I illustrate a perspective, cross-sectional view and a cross-sectional view, respectively, of the septum 510 being pressed further into the housing 505. As shown, a retaining edge 570, located at the top of the housing 505, may protrude into the lip mold 555. In its current state (as shown in FIG. 5I), the retaining edge 570 cannot effectively prevent the septum 510 from exiting the top of the cavity 520. However, the retaining edge 570 does allow the septum 510 to enter (or be pressed) into the cavity 520. Once the septum 510 is pressed into the cavity 520, the retaining edge 570 of the housing 505 may be melted as the horn 550 may supply heat, or heat may be introduced to the retaining edge 570. To facilitate the melting of the retaining edge 570, a plastic, polymer, or other material having a melting point below the melting points of the material of the septum 510 and the material of the horn 550 may be used. In this manner, the retaining edge 570 may be melted and molded into the lip mold 555 while retaining the integrity of the lip mold 555 and the septum 510. As a result, the retaining edge 570 is transformed into a different physical shape, thereby holding the septum 510 in place inside the cavity 520.

Figure 5J:
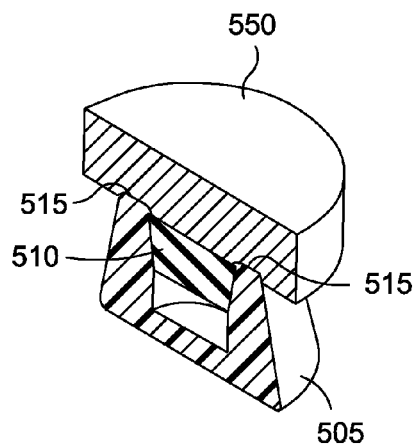
FIG. 5J illustrates a perspective, cross-sectional view of the injection port of FIG. 5A during a manufacturing process according to an embodiment of the present invention.
Figure 5K:
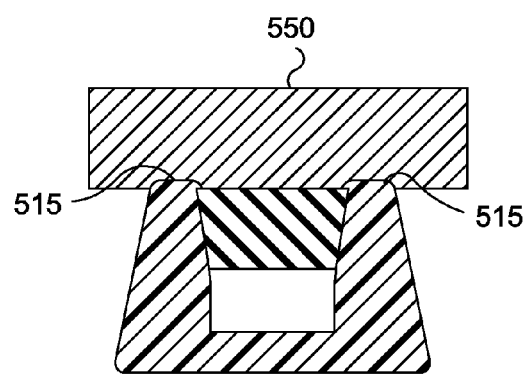
FIG. 5K illustrates a cross-sectional view of the injection port of FIG. 5A during a manufacturing process according to an embodiment of the present invention.

FIG. 5J and FIG. 5K illustrate a perspective, cross-sectional view and a cross-sectional view, respectively, of the retaining edge 570 having been transformed into the retaining lip 515 having an overhang portion which extends to contact and hold the septum 510 in place, thereby preventing the septum 510 from exiting the cavity 530 of the housing 505. The retaining lip 515 may also function to provide an axial load on the septum 510, which may cause an increase in radial compression exerted by the inner side wall 535.

Figure 5L:
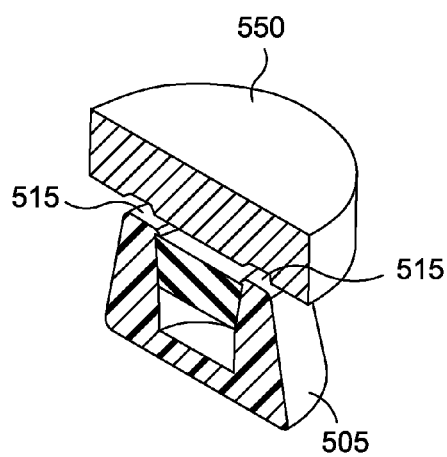
FIG. 5L illustrates a perspective, cross-sectional view of the injection port of FIG. 5A during a manufacturing process according to an embodiment of the present invention.
Figure 5M:
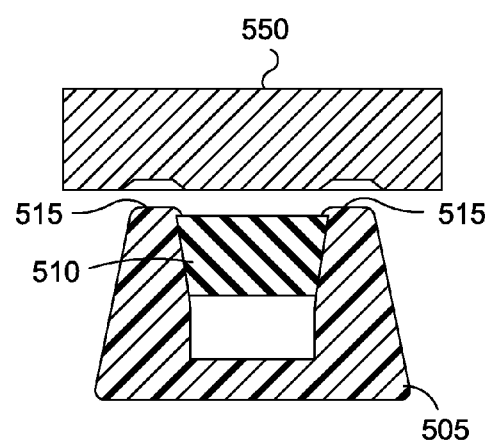
FIG. 5M illustrates a cross-sectional view of the injection port of FIG. 5A during a manufacturing process according to an embodiment of the present invention.

FIG. 5L and FIG. 5M illustrate a perspective, cross-sectional view and a cross-sectional view, respectively, of the manufactured injection port 500 with the horn 550 removed after the retaining lip 515 has cooled and hardened. In this manner, the injection port 500 may provide certain advantages over the prior art, such as reduced parts (the resulting injection port 500 has two distinct parts), simple molding of parts, and/or a simplified process for manufacturing a port/septum assembly.

Figure 6:
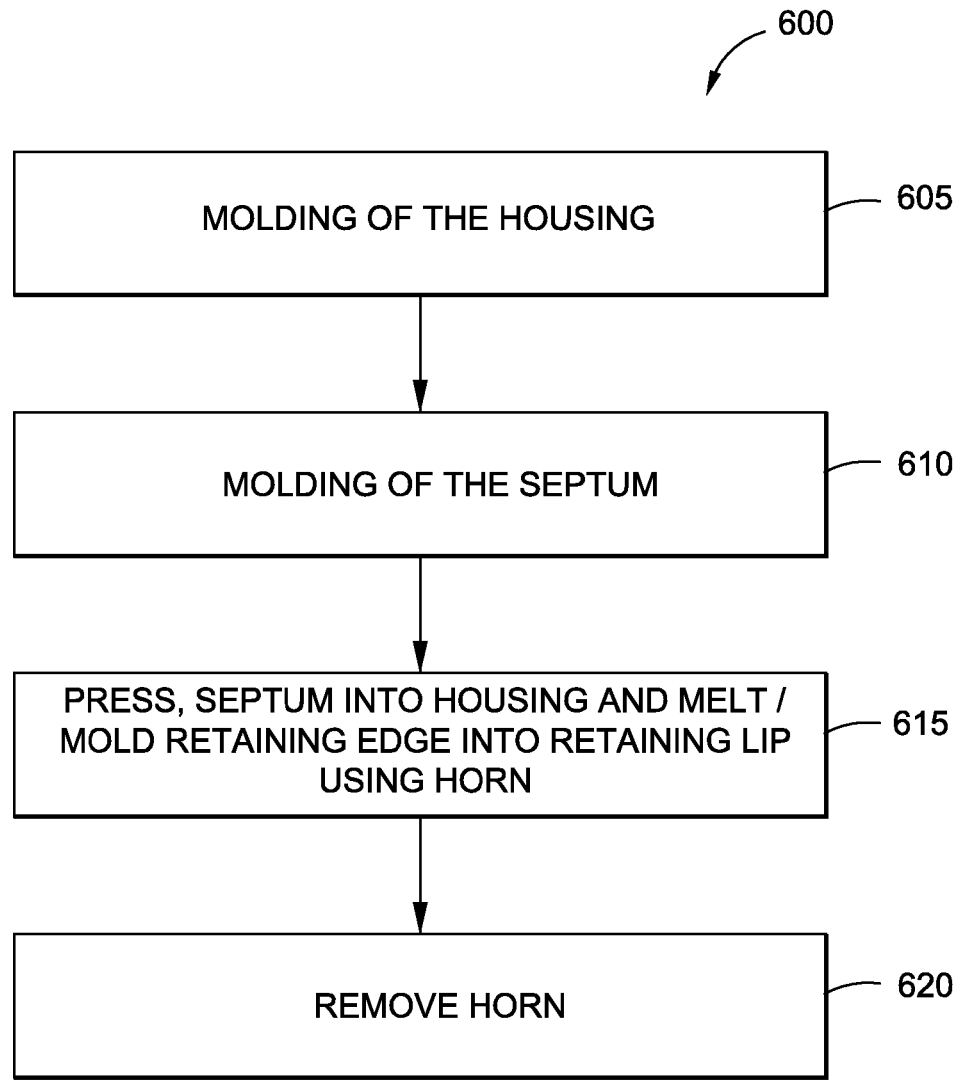
FIG. 6 illustrates a flow chart of the manufacturing process for the injection port of FIG. 5A according to an embodiment of the present invention.

FIG. 6 is a flow chart 600 of the manufacturing process for the injection port 500 of FIG. 5A. At step 605, the housing 505 for the injection port 500 may be molded. At step 610, the septum 510 may be molded. At step 615, the septum 510 may be pressed into the housing 505 by using the horn 550, and the retaining edge 570 of the housing 505 may be melted and molded into the lip mold 550 of the horn 550 resulting in the retaining lip 515. At step 620, after the retaining lip 515 hardens, the horn 550 may be removed, leaving the injection port 500. The assembly portion (e.g., step 615) comprises only one step, and accordingly, this approach may be considered a "one step process". Advantageously, by simplifying the process to manufacture an injection port, cost-savings and increased uniformity may be achieved.

FIG. 7A illustrates a septum-pressed injection port 700. Shown assembled, the injection port 700 may comprise two components: a housing 705 having septum-mating features and a septum 710 having conical retention features. The housing 705 may be plastic-molded and/or utilize any other moldable materials suitable for implantation into the human body. The septum 710 may be silicone-molded and/or may utilize any other moldable materials penetrable by a needle. The housing 705 and the septum 710 may be of geometric and appropriate tolerance design such that the septum 710 may be manually loaded into the housing 705 while simultaneously maintaining effective radial and axial compression. Also shown is a stem or a tubing-insertion access 755. In one embodiment, the injection port 700 may be the injection port 415 of FIG. 4.

FIG. 7B illustrates the septum 710 removed from the housing 705 to more clearly illustrate the geometry of the septum 710. As shown here, the septum 710 may have conical features including a retention ring 715 designed to hold the septum 710 within the housing 705, a needle-injection surface 720 designed to be penetrable by a needle, and a sealing surface 725 positioned between the needle-injection surface 720 and the retention ring 715 designed to further seal in fluid held within the housing 705 by the septum 710.

FIG. 7C is a cross-sectional view of the housing 705 without the septum 710 (the septum 710 being omitted in this FIG. for clarity of the features of the housing 705). The housing 705 may include a large cavity 730, being further divided into a top cavity 733 for holding the septum 710 and a bottom cavity 745 for carrying fluid (as the fluid reservoir). The top cavity 733 may be defined by a tapered side wall 750 positioned between a retention lip 735 and a retention protrusion 740. The retention lip 735 may be designed to overhang the retention ring 715 of the septum 710 when the septum 710 is correctly positioned within the top cavity 733. The retention protrusion 740 may be designed to protrude from the tapered side wall 750 defining a bottom retaining surface for contacting a bottom surface of the septum 710 and preventing the contacted portions of the bottom surface of the septum from extending beyond the retention protrusion when the retention lip 735 is overhanging and contacting the retention ring 715 of the septum 710, thereby preventing the septum 710 from moving into the bottom cavity 745. The bottom cavity 745 may be defined by a bottom side wall 760 which may have a channel or fluid conduit leading to the tubing-insertion access 755. As the housing 705 may be constructed out of a mold, one or more of the structural features of the housing 705 may be integrated into the physical structure of the housing 705.

FIG. 7D is a cross-sectional view of the septum 710 within the housing 705 and further clarifies how the features of the septum 710 mate with the features of the housing 705 to secure the septum 710 within the housing 705. As shown, the retention lip 735 overhangs and contacts a portion of the retention ring 715 of the septum 710 to prevent the septum 710 from exiting the cavity 733 of the housing 705 when the septum 710 is positioned within the cavity 733. The retention protrusion 740 may contact a bottom surface 726 of the septum 710 to prevent the septum 710 from moving into the bottom cavity 745, leaving the bottom cavity 745 free to carry fluid to and from the inflatable portion of the gastric band through the tubing-insertion access 755. In addition, when the septum 710 is held between the retention lip 735 and the retention protrusion 740, the septum 710 is radially compressed (by the tapered walls) and axially compressed (by the retention lip 735 and the retention protrusion 740), thereby enhancing the self-sealing features of the septum 710.

FIG. 8 illustrates an alternative embodiment of the pressed-septum injection port 700. In essence, the tubing-insertion access 755 is replaced by a tubing connector 855 molded and/or integrated into a housing 805 of the injection port 800. All other components of the injection port 800 including a septum 800 correspond with features discussed above in conjunction with the injection port 700.

The embodiments of FIGS. 7A-7D and FIG. 8 provide reduced cost by eliminating all but two components needed for an injection port, namely the housing and the septum while further reducing assembly costs during production by making it a one step process. Furthermore, assembly may be performed with manual operation or with a simple tool, thereby further reducing the need to design or utilize expensive machinery for assembly.

Figure 9:
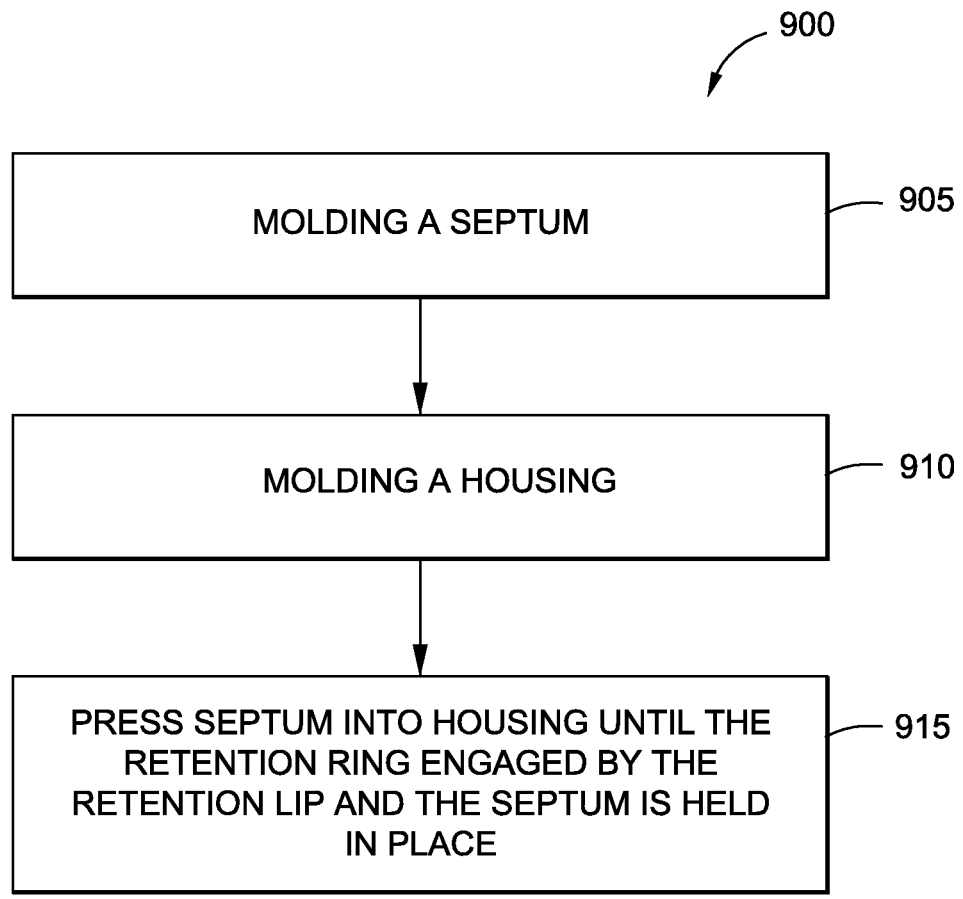
FIG. 9 illustrates a flow chart of the manufacturing process for the injection port of FIG. 7 according to an embodiment of the present invention.

FIG. 9 is a flow chart 900 of the manufacturing process for the injection port 700 of FIG. 7A and/or the injection port 800 of FIG. 8A. As shown, the manufacturing process 900 begins at step 905 with the molding of the septum into the shape illustrated in FIG. 7B. Next, at step 910, the housing is molded into the shape as shown in FIG. 7C. At step 915, once the septum and the housing are molded, the septum is pressed into the housing until the retention ring is engaged by the retention lip and the septum is held in place as shown in FIGS. 7A and 7D.

Figure 10A:
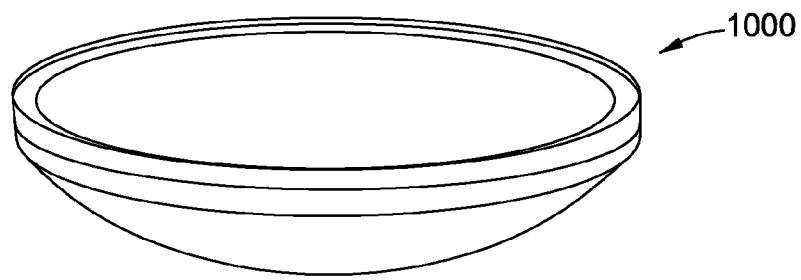
FIG. 10A illustrates a perspective view of an injection port according to an embodiment of the present invention.

FIG. 10A illustrates another embodiment of an injection port, and more particularly, showing a drum-shaped injection port 1000. The drum-shaped injection port 1000 may, in one embodiment, be shaped substantially similar to a hemisphere where the septum is located on the flat side, and not on the curved side. The drum-shaped injection port 1000 may provide the benefits of reduced production costs and improved reliability while maintaining the efficacy level common to current injection ports. The drum-shaped injection port 1000 may be assembled manually or with only a simple tool (e.g., to apply heat).

Figure 10B:
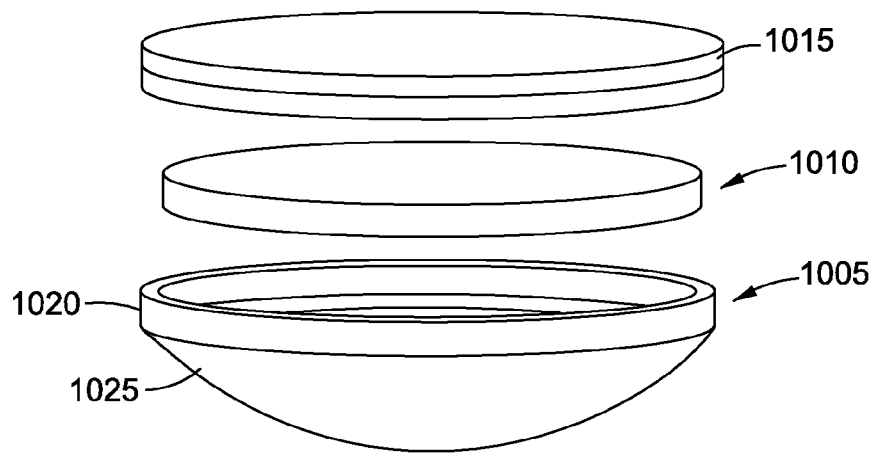
FIG. 10B illustrates a perspective view of the injection port of FIG. 10A with the septum and ring in a removed position according to an embodiment of the present invention.
Figure 10C:
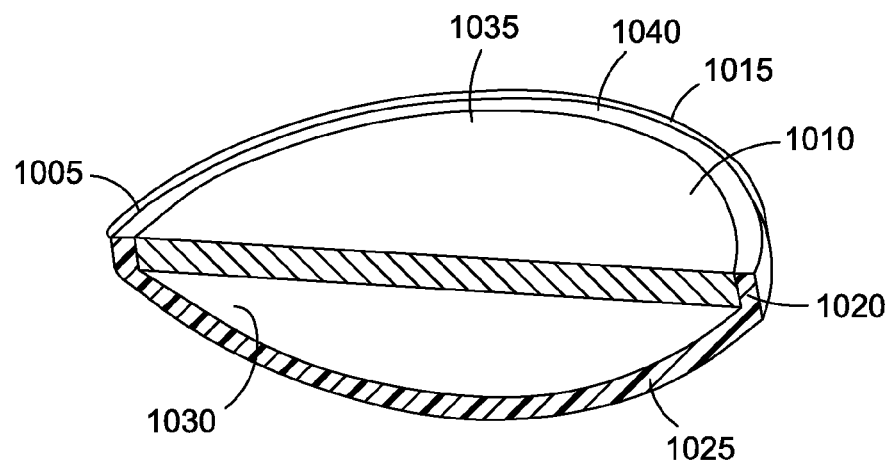
FIG. 10C illustrates a perspective, cross-sectional view of the injection port of FIG. 10A according to an embodiment of the present invention.

As further illustrated in the exploded view of the drum-shaped injection port 1000 of FIG. 10B and the cross-sectional view of FIG. 10C, the drum-shaped injection port 1000 may include a housing 1005 having a retaining ring 1020 (e.g., shaped as a circle or oval) defining an opening at the top of the housing 1005. The retaining ring 1020 may be integrated with a dome-shaped base which is configured to define a cavity or reservoir 1030 that holds the fluid. The drum-shaped injection port 1000 may also include a septum 1010 shaped to fit the opening of the retaining ring 1020 such that a top surface 1035 of the septum 1010 is flush with a top edge 1040 of the retaining ring 1020. The septum 1010 may be a biocompatible rubber or other biocompatible materials having self-sealing capabilities or properties having a diameter between about 1 centimeters (cm) and 8 centimeters (cm), but preferably between about 1 cm-about 5 cm. The retaining ring 1020 may define a first portion of a cavity having a diameter substantially equal to the diameter of the septum 1010. The first portion of the cavity may lead into a second portion of the cavity having an incrementally decreasing diameter moving away from the retaining ring 1020 in order to produce the drum or hemispherical shape of the injection port 1000 and span the top surface 1035 of the septum 1010.

In addition, the injection port 1000 may include a covering seal 1015 configured to fit the exterior of the retaining ring 1020. The covering seal 1015 may have a mesh or some other type of needle penetrable material to cover the septum 1010 and to assist the holding of the septum 1010 in place, and to help maintain septum integrity during internalized increased port pressure.

While not shown, a tubing connector could be molded into the drum-shaped injection port 1000 via side access or integrated into a reservoir defining wall 1025 of the housing 1005. By integrating the tubing connector into the mold, this concept has the flexibility of incorporating the tubing connection anywhere along the housing 1005.

Figure 11:
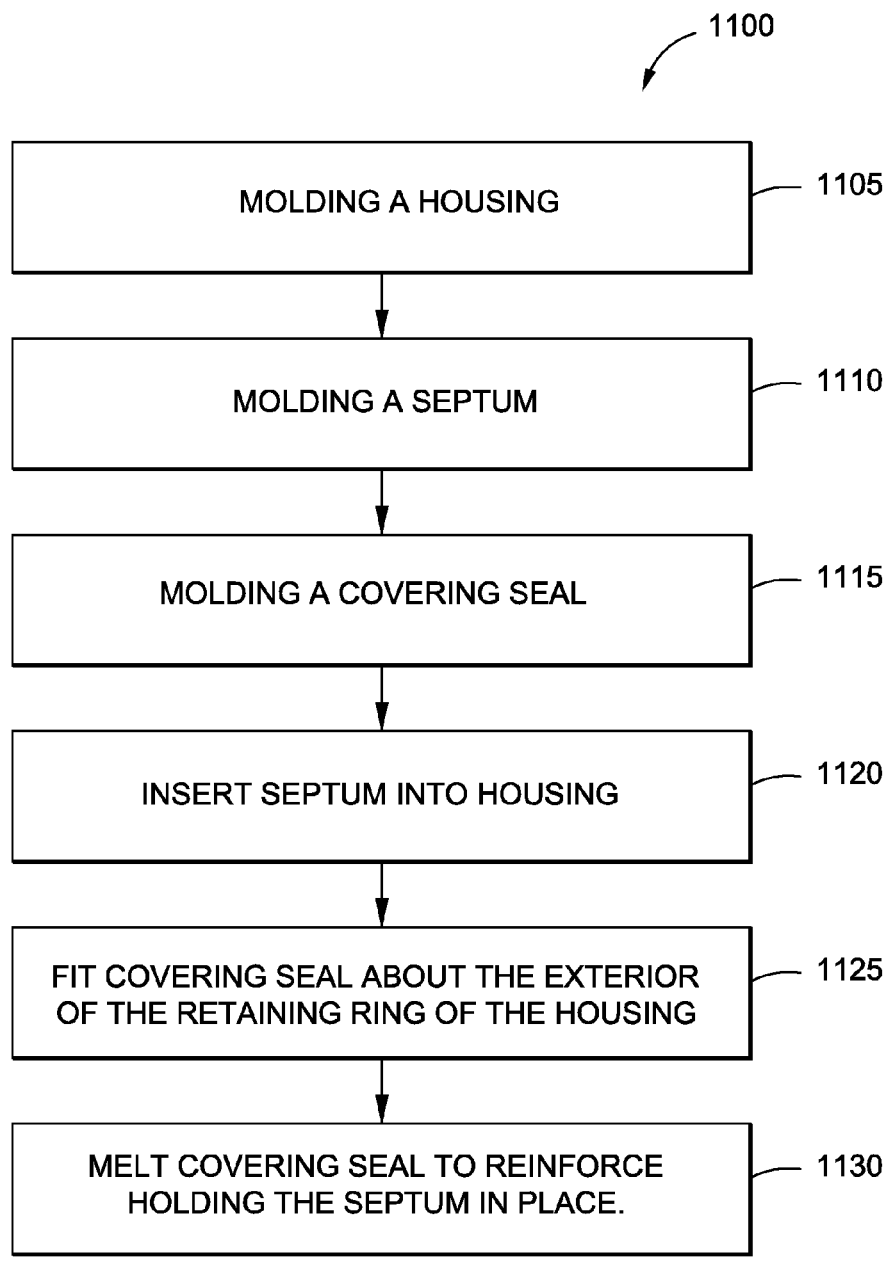
FIG. 11 illustrates a flow chart of the manufacturing process for the injection port of FIG. 10A according to an embodiment of the present invention.

FIG. 11 is a flow chart 1100 detailing one embodiment of to the manufacturing process of the drum-shaped injection port 1000 of FIGS. 10A-10C. At step 1105, the housing 1005 is molded out of biocompatible material such as a plastic or metal into the cup or drum shape with a low profile. Next, at step 1100, the septum 1010 may be molded out of a rubber to be in the shape of a disc and having a diameter to fit tightly into the retaining ring 1020 of the housing 1005. At step 1115, the covering seal 1015 may be molded out of a biocompatible plastic (e.g., a plastic with a lowering melting point than that of both the housing 1005 and the rubber septum 1010, and configured to fit about the exterior of the retaining ring 1020. Alternatively, the covering seal 1015 may be stamped, extruded, cut, woven, or braided, among other techniques.

Once the parts are constructed, then at step 1120, the septum 1010 may be inserted into the housing 1005 undergoing radial compression caused by interference with the retaining ring 1020. The septum 1010 should fit within the retaining ring 1020 in a flush manner and may be prevented from protruding into the cavity 1030 by the shape of the reservoir-defining wall 1025. In other words, because the reservoir-defining wall 1025 is shaped as a dome and gradually decreases in diameter as it moves away from the retaining ring 1020, the diameter of the septum 1010 causes it to be held in place. At step 1125, the covering seal 1015 may be pulled over the septum 1010 thereby forming a seal. The covering seal 1015 may be form fit over the exterior of the retaining ring 1020 as well, and in this manner, capping the drum-shaped injection port 1000. At step 1130, the covering seal 1015 may be thermally sealed circumferentially about the exterior of the retaining ring 1020 by utilizing a heating device to prevent leaks and to hold the septum 1010 in place. Alternatively, the covering seal 1015 may be crimpled, bonded or mechanically fixed to the housing 1005.

In one embodiment, the septum 1010 and the covering seal 1015 may be orientation-independent thereby further simplifying the manufacturing process. Furthermore, the resulting drum-shaped injection port 1000 has a low-profile which may be aesthetically acceptable to the patient while still providing a large surface area for needle penetration.

In one embodiment, the covering seal 1015 may be mesh-patterned to increase longevity and maintain integrity even after multiple needle injections.

Figure 12A:
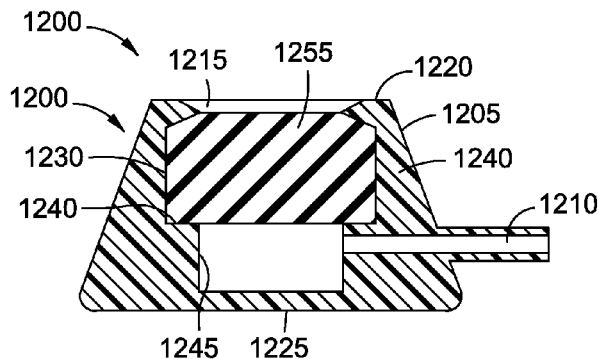
FIG. 12A illustrates a cross-sectional view of an injection port according to an embodiment of the present invention.

FIG. 12A illustrates a mold-in septum port 1200. Here, in this embodiment, a septum 1255 having self-sealing characteristics and properties may be molded into an already existing housing 1205, resulting in the mold-in septum port 1200.

Structurally, the housing 1205 may include a large cavity 1215, being further divided into a top cavity 1220 for holding the septum 1255 (shown in FIG. 12D) and a bottom cavity 1225 for carrying fluid (as the fluid reservoir). The top cavity 1220 may be defined by a top side wall 1230 positioned between a retention lip 1235 and a retention protrusion 1240. The retention lip 1235 may be designed to extend over the surface of the septum 1255 to prevent the septum 1255 from exiting out of the top of the mold-in septum port 1200 when the septum 1255 is correction positioned within the top cavity 1220. The retention protrusion 1240 may be designed to protrude from the top side wall 1230 and contact a bottom surface of the septum 1255, thereby preventing the septum from moving into the bottom cavity 1225. The bottom cavity 1225 may be defined by a bottom side wall 1245 which may have a channel or fluid conduit leading to a tubing-insertion access 1210. As the housing 1205 may be constructed out of a mold, all of the structural features of the housing 1205 may be integrated into the physical structure of the housing 1205.

The physical structure of the housing 1205 of the mold-in septum port 1200 having been described, attention will now be turned to the manufacturing of the mold-in septum port 1200 with respect to FIGS. 12B-D and FIG. 13.

Figure 12B:
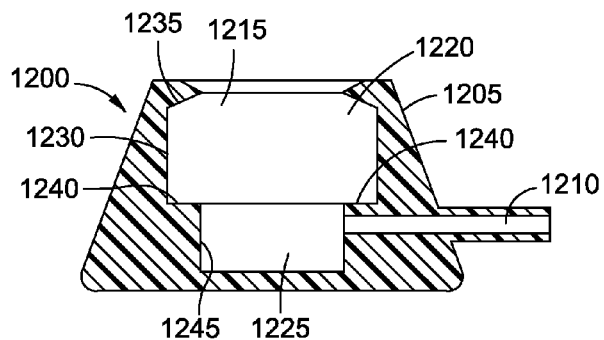
FIG. 12B illustrates a cross-sectional view of the housing of the access port of FIG. 12A according to an embodiment of the present invention.
Figure 12C:
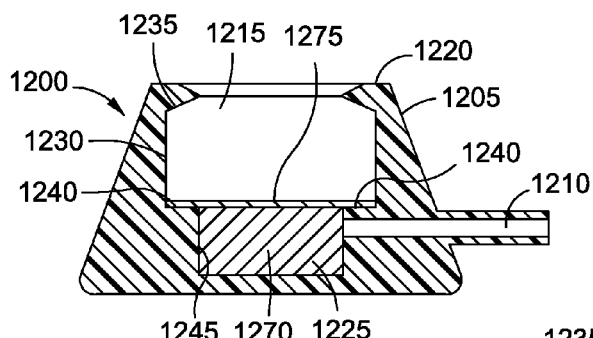
FIG. 12C illustrates a cross-sectional view of the housing, supporting material and a barrier of the injection port of FIG. 12A according to an embodiment of the present invention.
Figure 12D:
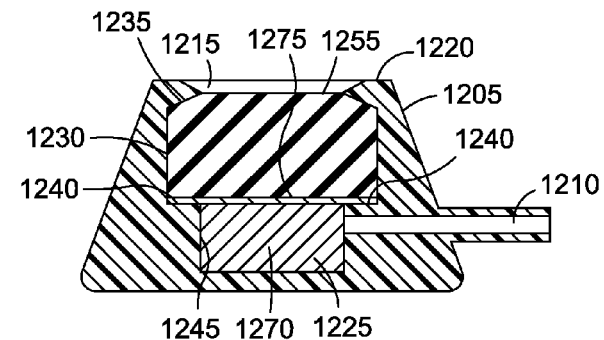
FIG. 12D illustrates a cross-sectional view of the housing, supporting material, barrier and septum of the injection port of FIG. 12A according to an embodiment of the present invention.
Figure 13:
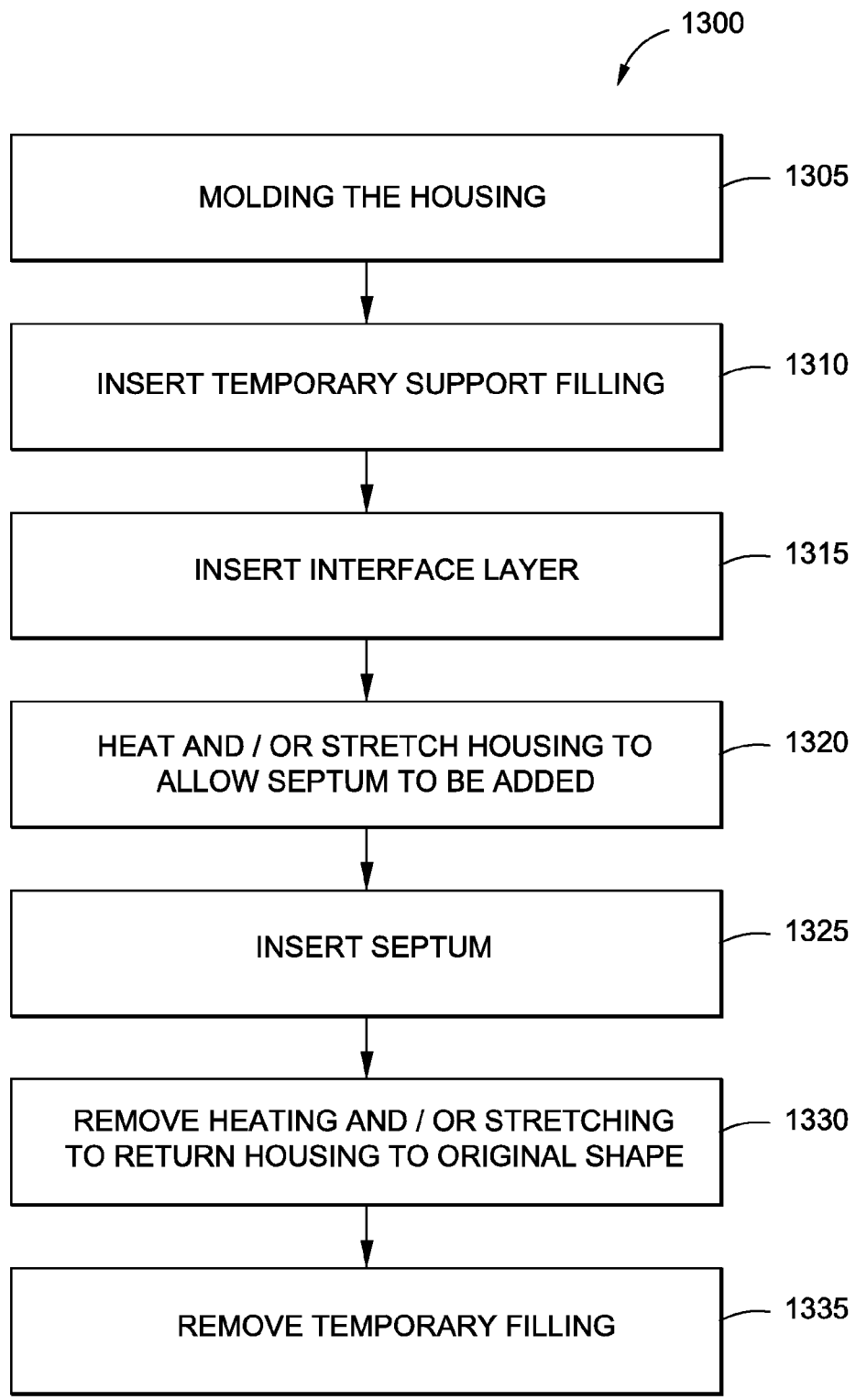
FIG. 13 illustrates a flow chart of the manufacturing process for the injection port of FIG. 12A according to an embodiment of the present invention.

As depicted in the flowchart of FIG. 13, at step 1305, the housing 1205 is molded, resulting in the "blank" housing 1205 of FIG. 12B. Once the housing 1205 is formed, the rest of the mold-in septum port 1200 may be assembled. At step 1310, and as shown in FIG. 12C, a temporary support filling 1270 such as an incompressible fluid, inflatable bladder and the like may be placed in the bottom cavity 1225 to prevent the later added silicone septum 1255 from sinking into the bottom cavity 1225. If desired, at step 1315, an interface layer 1275 designed to be needle-penetrable may be inserted on top of the temporary support material. After the temporary support filling 1270 is inserted to fill the bottom cavity 1225 of the housing 1205, the septum 1255 may now be inserted. At step 1320, the housing 1205 with the temporary support filling 1270 is placed in a molding machine and heated and/or stretched out to increase the inner diameters of the housing 1205. Next, at step 1325, the septum 1255 is inserted via the diameter-expanded opening of the housing 1205 and molded under compression. Then at step 1330, the heating or stretching of the housing 1205 is removed, thereby returning the housing to its original shape (with a smaller diameter of the openings, etc.) to fix the septum 1255 in place and further, to provide the septum 1255 with radial and axial compression to enhance the self-sealing capabilities of the septum 1255. The result of step 1330 is illustrated by FIG. 12D.

At step 1335, the temporary support filling 1270 may be removed (e.g., through the tubing connector 1210) to result in the assembled mold-in septum port 1200 as depicted in FIG. 12A.

Figure 14A:
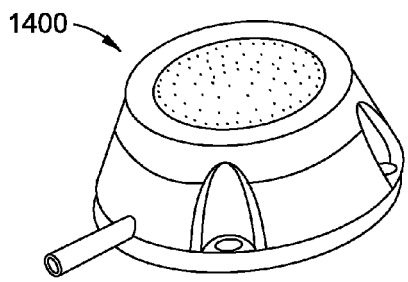
FIG. 14A illustrates a top perspective view of an access port according to an embodiment of the present invention.
Figure 14B:
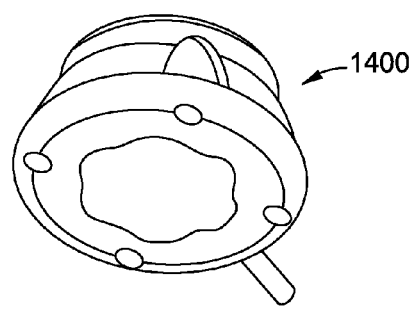
FIG. 14B illustrates a bottom perspective view of the access port of FIG. 19A according to an embodiment of the present invention.
Figure 14C:
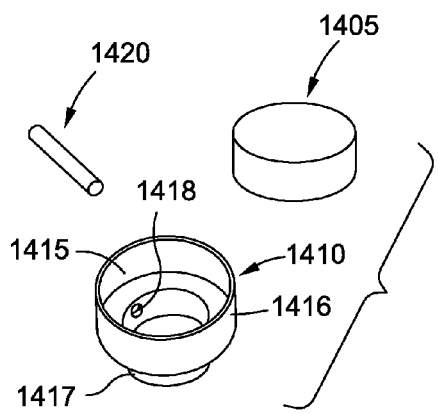
FIG. 14C illustrates certain components and a mold for constructing the access port of FIG. 14A according to an embodiment of the present invention.
Figure 14D:
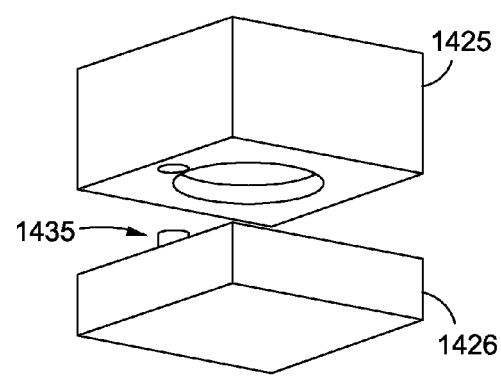
FIG. 14D illustrates a placement of certain components within a mold for constructing an access port according to an embodiment of the present invention.
Figure 14E:
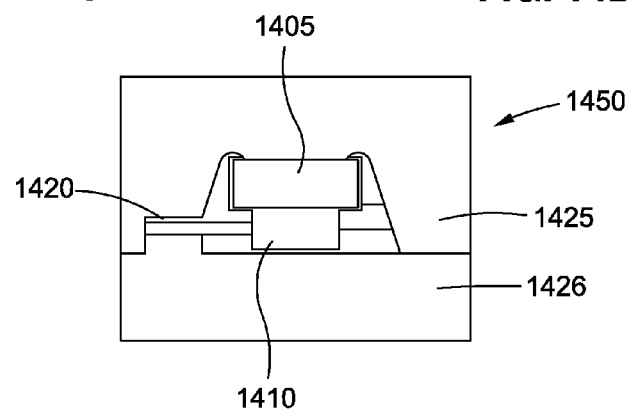
FIG. 14E illustrates the placement of the components within the mold for constructing the access port of FIG. 14A according to an embodiment of the present invention.

As an alternative, an over-molded port 1400 as depicted in FIGS. 14A and 14B may provide for a completely sealed port encapsulated in solid material. Generally, a septum 1405, a compression ring 1410 defining a reservoir 1415 and a stem insert or tube connector 1420, as shown in FIG. 14C may be assembled in a top mold 1425 and the bottom mold 1426 of FIG. 14D to result in the assembly 1450 of FIG. 14E. The septum 1405 may include a top surface, a bottom surface and a side wall for joining the top surface and the bottom surface. The compression ring 1410 may receive the septum 1405 and further define a reservoir 1415 and may include a ring portion 1416 for holding the septum 1405 in place, and a reservoir defining portion 1417 integrated with the ring portion 1416, the reservoir defining portion 1417 having a stem insert or connector interface 1418 (e.g., a hole or a port).

Referring back to FIG. 14D, the mold 1450 may allow for the injection of the biocompatible material (e.g., titanium) to form the housing and encapsulate a portion of the septum 1405, the compression ring 1410 and the stem insert 1420. The top mold 1425 may include a void or spacing designed to be filled by an injected biocompatible material such as titanium to form the housing of the over-molded port 1400. The bottom mold 1426 may include a stem holder 1435 designed to hold the stem insert or tube connector 1420. In one embodiment, the spacing in the top mold 1425 and the bottom mold 1426 to formulate the housing may provide radial compression to the septum 1405 once the biocompatible material to be used as the housing is injected into and/or molded over the septum 1405, the compression ring 1410 and the stem insert or tube connector 1420. Furthermore, in one or more embodiments, intentional voids can be left in the over-molded plastic to reduce the use of implantable materials to save on costs. These voids could be filled, left open or designed with features to promote tissue in-growth at the base of the over-molded port 1400.

Referring back to the compression ring 1410, in one embodiment, a high durometer (shore A durometer of 70 or greater) material may be used to construct the compression ring 1410.

Figure 15:
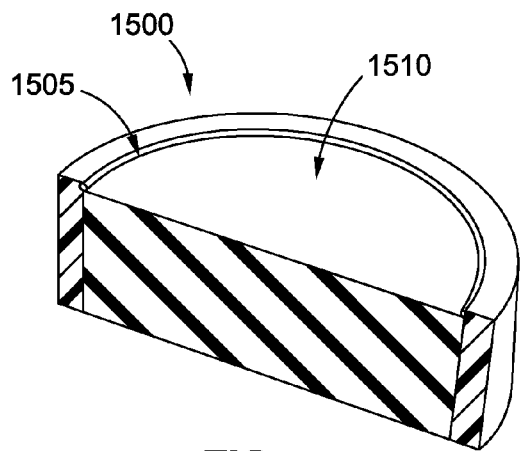
FIG. 15 illustrates a perspective, cross-sectional view of a pre-compressed septum having a compression ring according to an embodiment of the present invention.

FIG. 15 illustrates one example of a cross-sectional view of a stretched-on compression assembly 1500, which in one embodiment, may be utilized as the compression ring 1410 of the over-molded port 1400 of FIG. 14A. Here, the compression ring 1505 may surround a previously-cured septum 1510 by being stretched around or compression-molded onto the outside of the septum 1510 to create the stand-alone radially compressed septum.

Figure 16:
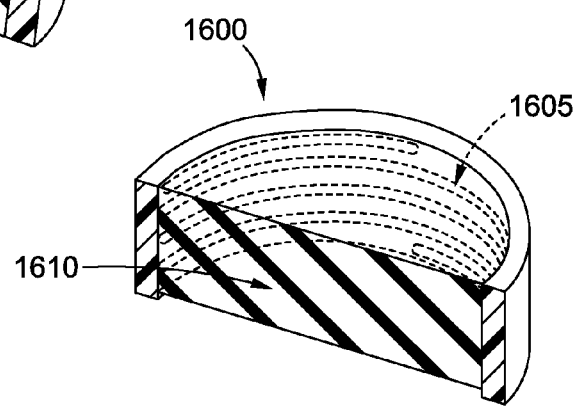
FIG. 16 illustrates a perspective, cross-sectional view of a pre-compressed septum having a compression coil according to an embodiment of the present invention.

FIG. 16 illustrates an alternative compression ring assembly 1600 which may be incorporated as the compression ring 1410 of the over-molded port 1400 of FIG. 14A. More particularly, as shown in FIG. 16, a ring structure 1605 constructed out of a memory material (e.g., a nitinol compression coil) may be utilized as the compression ring and molded into the silicone rubber septum 1610. Compression may be effected by heating the memory material to return the memory material to its memory state thereby radially compressing the silicone rubber septum 1610.

Figure 17:
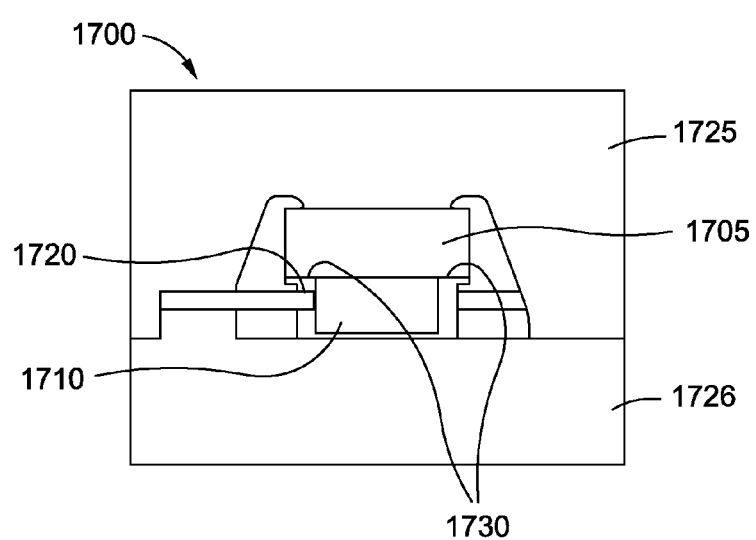
FIG. 17 illustrates the placement of certain components, excluding a compression ring, within a mold for constructing the access port of FIG. 14A according to an embodiment of the present invention.

A variation of the over-molded port 1400 of FIG. 14A which does not require a compression ring is illustrated in FIG. 17. While the resulting over-molded port 1700 may appear similar to the over-molded port 1400 of FIG. 14A, the top and bottom molds 1725, 1726 and certain component parts (the reservoir 1710) are modified. For example, the compression ring portion of the analogous component (compression ring and reservoir 1410) has been removed, resulting in only the "reservoir 1710". The reservoir 1710 may include septum supporting structures 1730 to suspend a septum 1705 in place above the reservoir 1710. In this embodiment, the pressure of the injected material to form the housing may provide radial compression on the septum 1705.

Figure 18A:
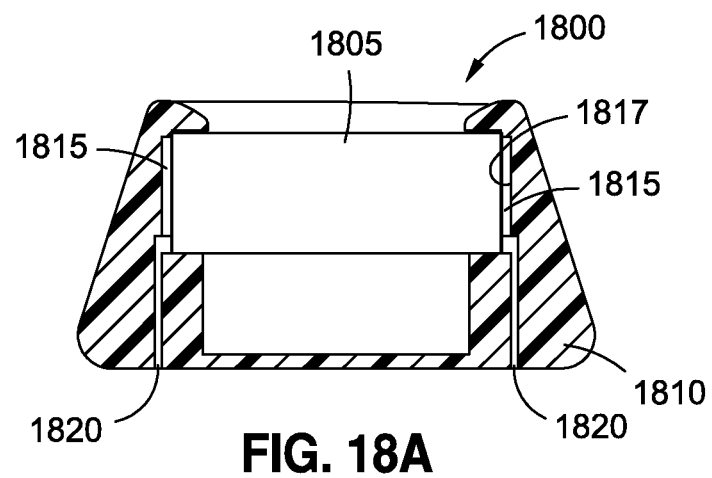
FIG. 18A illustrates a cross-sectional view of a septum inside an access port housing prior to compression injections according to an embodiment of the present invention.

The concept of using the injection process to provide compression may be modified and applied to other injection ports. For example, FIG. 18A illustrates an injection port 1800 having a septum 1805 inserted into a housing 1810. Compression on the septum 1805 may be provided by injecting a compression providing substance, for example, liquid silicone injections 1815 under pressure after the septum 1805 is already inserted into the housing 1810 without the desired amount of compression. In this particular embodiment, vents 1820 may be left to seal the injection port 1800. This type of construction of the injection port 1800 may be considered a post-injected silicone compressed septum assembly.

Figure 18B:
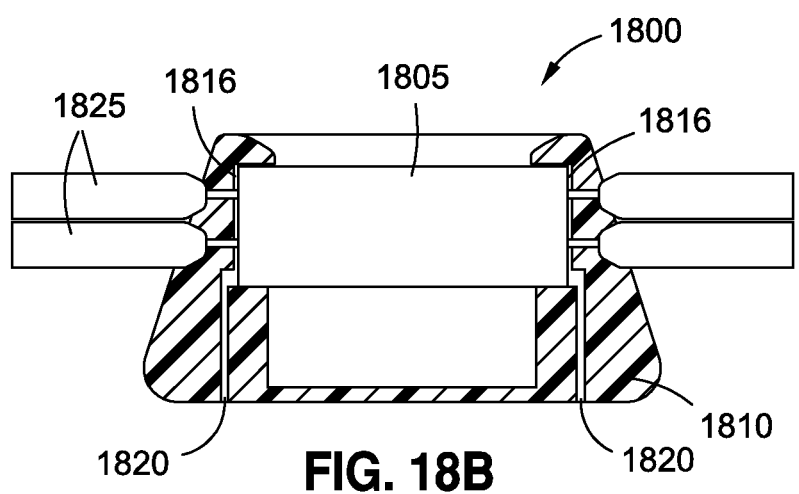
FIG. 18B illustrates a cross-sectional view of injection nozzles providing compression injections to compress a septum housed inside an access port housing of FIG. 18A according to an embodiment of the present invention.

FIG. 18B illustrates injection nozzles 1825 which may be used to provide the liquid silicone injections into a gap 1816. In this manner, the septum 1805 may be radially compressed. The compression of the septum 1805 improves the sealing of the injection port 1800 and also provides the benefit of improving the self-sealing characteristics of the septum 1805 after the septum 1805 is punctured with a needle.

In one embodiment, manufacturing the injection port 1800 may comprise molding a housing 1810 to include an opening at a top of the housing 1810 leading into a cavity defined by an inner side wall 1817 of the housing 1810 and an inner bottom wall of the housing 1810, the cavity having a first portion and a second portion, the first portion of the cavity being positioned between the opening and the second portion of the cavity. Next, a septum 1805 may be inserted into the first portion of the cavity leaving a gap 1815 between an exterior of the septum 1805 and the inner side wall. Then, radial compression exerted on the septum 1805 may be increased by adding liquid silicone or other appropriate substances to fill the gap 1815 between the exterior of the septum 1805 and the inner side wall of the housing 1810 via injection. That is, liquid silicone may be injected into the gap 1815 using injection nozzles inserted into openings that extends from the side of the housing 1810 into the gap 1815.

FIG. 19A illustrates a dome-shaped port 1900 which may be, in one embodiment, include a compressed septum (e.g., formed from a silicone from a membrane) located in a housing to form a hemispherically-shaped object. The dome-shaped port 1900 may advantageously incorporate the compressive effect that bending has on materials to create a compressed silicone septum 1905 located in a housing 1910. To construct the dome-shaped port 1900, a flat piece of silicone-sheeting 1901 (as shown in FIG. 19B) with woven mesh adhered to one side may be used. The silicone-sheeting 1901 may originally be a disc, and may be integrated with a mesh 1902. As the silicone-sheeting 1901 is forced into a dome shape, the silicone-sheeting 1901 may be structurally held in the dome shape with the mesh 1902 on the outside to maintain the compression to seal against needle punctures as shown in FIG. 19C.

Structurally, the housing 1910 may include a substantially circular cut-out portion defined by a circumferential edge 1906 (for exposing the septum to a needle), a bottom surface having 1908 a diameter larger than the circumferential edge 1906, and a curved side wall 1907 extending from the circumferential edge 1907 to the bottom surface 1908.

In one embodiment, barbs (not shown) may be designed in the mesh 1902 to hold it in place when the injection port 1900 is under pressure.

As an alternative, the silicone-sheeting 1901 may be molded into an inverted dome. When the inverted dome is flipped and assembled into the housing 1910, the compression may be doubled to that of the flat-disc formed into the dome shape.

Various port assemblies now having been described, attention will be turned to certain features which may be added to any port assembly, whether described herein or not, to further improve the performance of the port assembly.

In one embodiment, a lip seal may be incorporated into a septum to improve reservoir sealing under pressure. The lip seal may still allow for improved needle puncture sealing. For example, FIG. 20 illustrates an injection port 2000 having a lip seal 2005 integrated into the septum 2010. When the lip seal 2005 is pressed against a reservoir wall 2015 as the fluid increases in a cavity 2020 (e.g., in response to pressure increase caused by the added fluid), the sealing capacity or ability of the lip seal 2005 also increases, thereby preventing leaks around the septum 2010.

In addition to lip seals, a softer tubing connection may be incorporated to prevent premature wearing of the connected tubing to an injection port and reduce or eliminate the need for titanium stems or bulky strain reliefs to protect the tubing. Softer tubing connections may avoid the use of harder materials and protruding stems (although the user of harder materials is still possible if needed).

Typically, a stem may be load-concentrated at an unprotected and minimally supported portion. For example, FIG. 21 illustrates a tubing connector 2100 load concentrated at arrow 2105. By having the load concentrated as such a point, the connector failure rate is adversely increased. Indeed, this is the source of most connector failures.

By sinking the tubing connector as shown in FIGS. 22 and 23, the load may be diverted from the tip of the connector.

FIG. 22 illustrates a sunken connector 2200 having an exit that is radiused at location 2210 to further prevent a concentrated load on the sunken connector 2200. The connector 2200 is "sunken" into or partially inserted into the access port housing itself. In other words, a first portion of the sunken connector 2200 is located inside the access port housing while a second portion of the sunken connector 2200 is located outside of the access port housing and leading to the tubing. By configuring the connector 2200 to be insertable into the housing, the load is diverted away from the tip of the connector 2200 and supported by not only the tip of the connector 2200 but also by the portion of the access port housing surrounding the top of the connector 2200.

Alternatively, and/or in addition, a sunken connector 2300 may be utilized with a strain relief mechanism 2305. Similar to connector 2200, connector 2300 is insertable into the access port housing itself. Here, the strain relief mechanism 2305 may appear as wings or protrusions that partially or fully fill the opening of the access port to provide strain relief.

Figure 24:
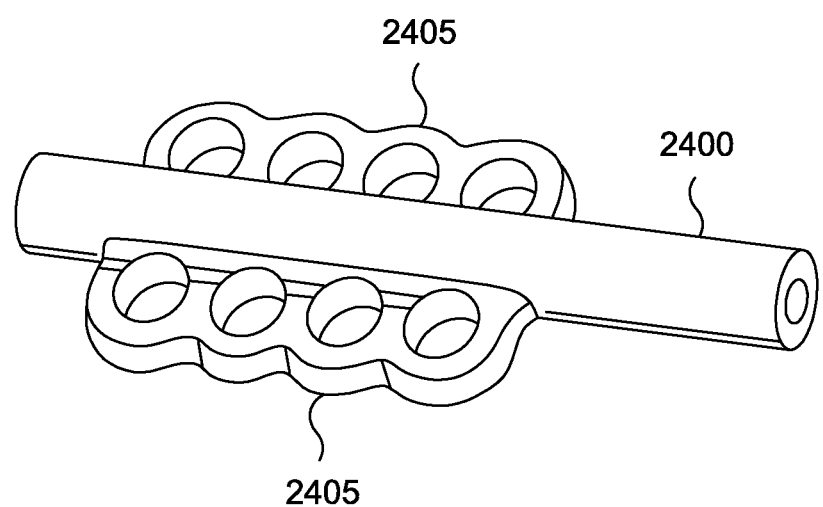
FIG. 24 illustrates a tubing having rings according to an embodiment of the present invention.

The port connector may further be enhanced to provide additional benefits to the patient. For example, a tubing connector 2400 of FIG. 24 may include in-growth features 2405 to create proper fixation of an injection port to a patient's tissues. Such in-growth features 2405 may be added to the tubing connector 2400 or tubing as a means of attachment rather than sutures, anchors or mesh. These in-growth features 2405 may come in many forms such as pores, hole-filled, or other configurations to encourage integration into the patient's bodily tissues. In this particular embodiment, the in-growth features 2405 may be two sets of four integrated holes on either side of the tubing connector 2400. However, the actual number and/or configuration of the holes may be altered as desired.

Unless otherwise indicated, all numbers expressing quantities of ingredients, volumes of fluids, and so forth as used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, certain references have been made to patents and printed publications throughout this specification. Each of the above-cited references and printed publications are individually incorporated herein by reference in their entirety.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. An injection port for use with a gastric band for the treatment of obesity, the injection port implantable in a patient and coupled to a tube that is connected to an inflatable portion of the gastric band, the injection port comprising:
    a septum having a top surface, a bottom surface, and a side wall connecting the top surface to the bottom surface; and
    a housing configured to receive and secure the septum, the housing including:
        a first inner side wall being tapered inwards such that an opening defined at a first end is larger than an opening defined at a second end, the tapering of the first inner side wall being used to secure the septum within the housing, the first inner side wall being continuously tapered from the first end to the second end, and the first end extending to the top surface of the septum,
        a second inner side wall having a first end and a second end, the first end of the second inner side wall joined to the second end of the first inner side wall, the second inner side wall having an opening in fluid communication with the tube,
        a closed bottom surface joined to the second end of the second inner side wall, and wherein the first inner side wall, the second inner side wall and the bottom surface define a cavity in fluid communication with the tube having at least two portions, a first portion of the cavity defined by the first inner side wall and for receiving the septum and allowing the first inner side wall to secure the septum by axially exerting compression on the septum, and a second portion of the cavity defined by the second inner side wall and the bottom surface, the second portion of the cavity for holding a fluid, and
        a retaining lip joined to the first end of the first inner side wall and for securing the top surface of the septum.

2. The injection port of claim 1 wherein the septum has a diameter that is greater than a diameter of the second portion of the cavity.

3. The injection port of claim 1, wherein the septum is radially and axially compressed when retained in the first portion of the cavity.

* * * * *